United States Patent
Martinez Chantar et al.

(10) Patent No.: US 10,457,941 B2
(45) Date of Patent: Oct. 29, 2019

(54) METHODS AND COMPOSITIONS TO TREAT LIVER DISEASES AND CONDITIONS

(71) Applicant: Asociacion Centro de Investigacion Cooperativa en Biociencias-CIC bioGUNE, Derio (ES)

(72) Inventors: Maria Luz Martinez Chantar, Derio (ES); Juan Anguita, Derio (ES)

(73) Assignee: Asociacion Centro de Investigacion Cooperativa en Biociencias-CIC bioGUNE, Derio (ES)

( * ) Notice: Subject to any disclaimer, the term of this patent is extended or adjusted under 35 U.S.C. 154(b) by 0 days.

(21) Appl. No.: 15/753,461

(22) PCT Filed: Aug. 20, 2016

(86) PCT No.: PCT/IB2016/001275
§ 371 (c)(1),
(2) Date: Feb. 19, 2018

(87) PCT Pub. No.: WO2017/029556
PCT Pub. Date: Feb. 23, 2017

(65) Prior Publication Data
US 2018/0245080 A1    Aug. 30, 2018

Related U.S. Application Data

(60) Provisional application No. 62/207,456, filed on Aug. 20, 2015.

(51) Int. Cl.
| | |
|---|---|
| *A61K 48/00* | (2006.01) |
| *C07H 21/04* | (2006.01) |
| *C12N 15/113* | (2010.01) |
| *A61K 31/7088* | (2006.01) |
| *A61K 45/06* | (2006.01) |
| *G01N 33/50* | (2006.01) |

(52) U.S. Cl.
CPC ........ *C12N 15/113* (2013.01); *A61K 31/7088* (2013.01); *A61K 45/06* (2013.01); *C12Y 201/0102* (2013.01); *G01N 33/502* (2013.01); *G01N 33/5067* (2013.01); *C12N 2310/113* (2013.01); *C12N 2310/141* (2013.01); *C12N 2310/531* (2013.01); *C12N 2320/31* (2013.01)

(58) Field of Classification Search
CPC .. A61K 31/713; C12N 2310/11; C12N 15/111
See application file for complete search history.

(56) References Cited

U.S. PATENT DOCUMENTS

2011/0293653 A1    12/2011    Szabo et al.

FOREIGN PATENT DOCUMENTS

WO    2013/153082 A1    10/2013

OTHER PUBLICATIONS

Avila et al., "Reduced mRNA abundance of the main enzymes involved in methionine metabolism in human liver cirrhosis and hepatocellular carcinoma." Journal of Hepatology (2000) 33: pp. 907-914.
Baigude et al., "Strategies to antagonize miRNA functions in vitro and in vivo." Nanomedicine (Lond.), (2014) 9(16), 2545-2555.
Barbier-Torres et al., "Stabilization of LKB1 and Akt by neddylation regulates energy metabolism in liver cancer." Oncotarget, vol. 6, No. 4, 2509-2523.
Bligh & Dyer, "A Rapid Method of Total Lipid Extraction and Purification." Can. J. Biochem. Physiol, (Aug. 1959); vol. 37(8): pp. 911-917.
Chen et al. "Novel materials which possess the ability to target liver cells." Expert Opinion, Drug Deliv. (2012) 9(6):649-656.
Croce, C.M., "Molecular Origins of Cancer, Oncogenes and Cancer." N. Engl. J. Med., (2008); 358:502-511.
Czech. Michael, P. "MicroRNAs as Therapeutic Targets." New England Journal of Medicine, 354;11.
Ebert et al., "MicroRNA sponges: competitive inhibitors of small RNAs in mammalian cells." Nat. Methods, (2007), (9):721-6.
Embade et al., "Murine Double Minute 2 Regulates Hu Antigen R Stability in Human Liver and Colon Cancer Through NEDDylation." (2012) J. Hepatol; 55:1237-1248.
Esau, Christine C., "Inhibition of microRNA with antisense oligonucleotides." ScienceDirect, Methods 44 (2008) 55-60.
Fernandez-Alvarez et al., "Trail-producing NK cells contribute to liver injury and related fibrogenesis in the context of GNMT deficiency." Laboratory Investigation (2015) 95, 223-236.
Flipowicz, et al., "Post-transcriptional gene silencing by siRNAs and miRNAs." Current Opinion in Structural Biology 2005, 15:331-341.
Huidobro et al., "A DNA methylation signature associated with the epigenetic repression of glycine N-methyltransferase in human hepatocellular carcinoma." J. Mol. Med. (2013) 91:939-950.
Hung et al., "MicroRNA-224 down-regulates Glycine N-methyltransferase gene expression in Hepatocellular Carcinoma." Scientific Reports, (2018), 8:12284, 1-14. J Mol Med (2013) 91:939-950.
International Search Report and Written Opinion from corresponding PCT Application No. PCT/IB2016/001275.
Jung & Kullak-Ublick, "Hepatocyte Nuclear Factor 1a: A Key Mediator of the Effect of Bile Acids on Gene Expression." Hepatology, vol. 37, No. 3, 2003, 622-631.
Krutzfeldt et al.,"Silencing of microRNAs in vivo with 'antagomirs'." NATURE|vol. 438|Dec. 1, 2005 686.
Le et al., "A sensitive mass spectrometry method for simultaneous quantification of DNA methylation and hydroxymethylation levels in biological samples." Analytical Biochemistry 412 (2011) 203-209.
Li et al., "Targeted delivery of drugs for liver fibrosis." Expert Opin. Drug Deliv. (2009) 6(5).
Liao et al., "Glycine N-Methyltransferase Deficiency Affects Niemann-Pick Type C2 Protein Stability and Regulates Hepatic Cholesterol Homeostasis." Molecular Medicine, vol. 18, 412-422 (2012).

(Continued)

*Primary Examiner* — Amy H Bowman
(74) *Attorney, Agent, or Firm* — Pierce Atwood LLP

(57) ABSTRACT

Methods and compounds useful to treat diseases and conditions are provided. Methods of administering one or more microRNA-inhibitor compounds or one or more microRNA-enhancing compounds to cells, tissues, and/or subjects as a treatment for a disease or condition are provided.

14 Claims, 22 Drawing Sheets

Specification includes a Sequence Listing.

(56) References Cited

OTHER PUBLICATIONS

Mann et al., "Epigenetics in Liver Disease." (2014) 60: 1418-1425.
Mann et al., "MeCP2 Controls an Epigenetic Pathway That Promotes Myofibroblast Transdifferentiation and Fibrosis." Gastroenterology (2010) 138: 704-714, 714.e1-4.
Martinez-Chantar et al., "Loss of the Glycine N-Methyltransferase Gene Leads to Steatosis and Hepatocellular Carcinoma in Mice." J. of Heptol. (2008); 47: pp. 1191-1199.
Martinez-Lopez et al., "Hepatoma Cells From Mice Deficient in Glycine N-Methyltransferase Have Increased RAS Signaling and Activation of Liver Kinase B1." Gastroenterology, (2012), 143: 787-798.
Martinez-Una et al. "Excess S-adenosylmethionine Reroutes Phosphatidylethanolamine Towards Phosphatidylcholine and Triglyceride Synthesis." Hepatology, vol. 58, No. 4, (2013), 2196-1305.
Martinez-Una et al. "S-Adenosylmethionine increases circulating very-low density lipoprotein clearance in non-alcoholic fatty liver disease." Hepatology, (2015), vol. 62, 673-681.
Meltzer, P.S., "Small RNAs with big impacts." Nature, (2005), vol. 435: 745-746.
Michelotti et al. "NAFLD, NASH and liver cancer." Nature Reviews, Gastroenterologuy & Hepatology, vol. 10, Nov. 1, 2013, pp. 656-665.
Pathak et al., "Polyimide-polyethylene glycol block copolymers: Synthesis, characterization, and initial evaluation as a biomaterial." Journal of Biomaterials Science, Polymer Edition, 6:4, 313-323.
Poelstra et al., "Drug targeting to the diseased liver." Journal of Controlled Release 161 (2012) 188-197.
Tay et al., "Using artificial microRNA sponges to achieve microRNA loss-of-function in cancer cells." ADR-12610; No. of pp. 11.
Varela-Rey, et al., "Impaired Liver Regeneration in Mice Lacking Glycine N-Methyltransferase." J. of Hepatol. (2009), 5:2, 443-452.
Villa et al.,"Neoangiogenesis-related genes are hallmarks of fast-growing hepatocellular carcinomas and worst survival. Results from a prospective study." Gut (2015);0: 1-9.
Wagner et al., "Hepatocellular carcinoma in GNMT−/− mice." Toxicology and Applied Pharmacology 237 (2009) 246.
Yen et al., "Glycine N-methyltransferase affects the metabolism of aflatoxin B1 and blocks its carcinogenic effect." Toxicology and Applied Pharmacology 235 (2009) 296-304.

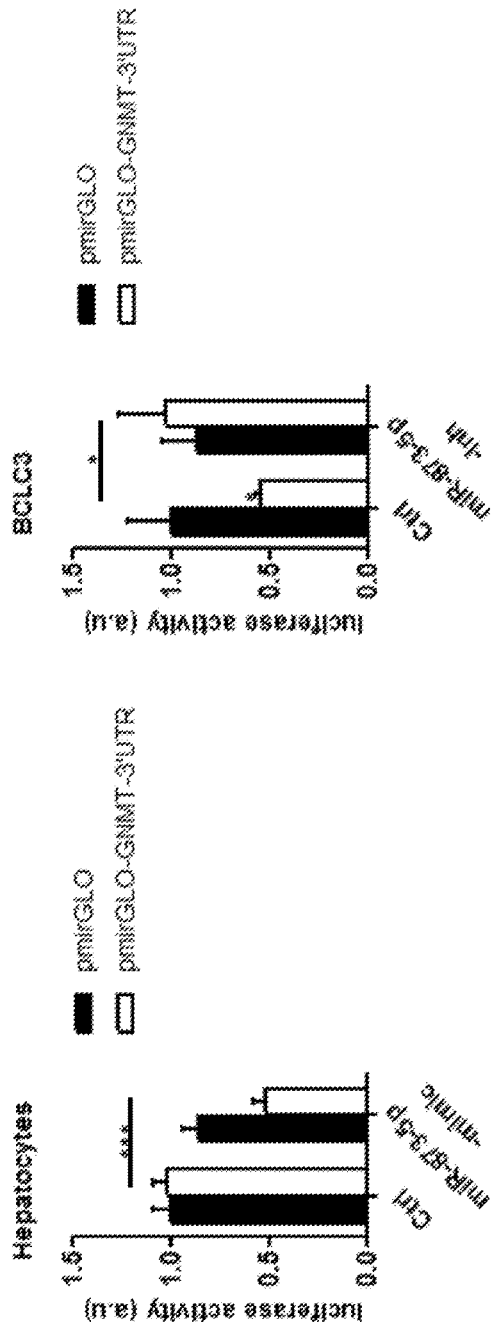
Fig. 1D
Fig. 1E
Fig. 1F

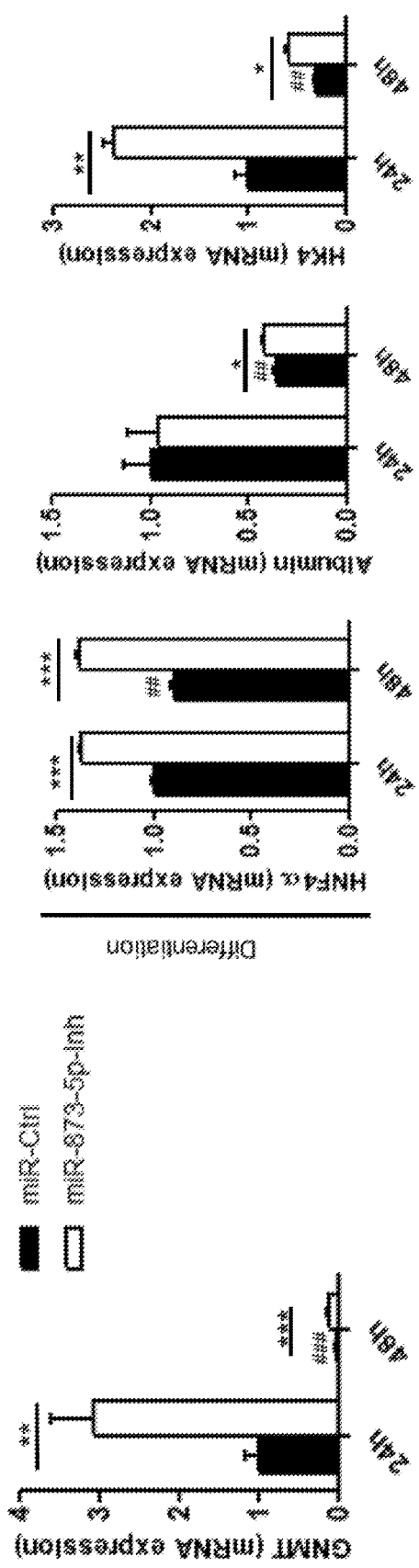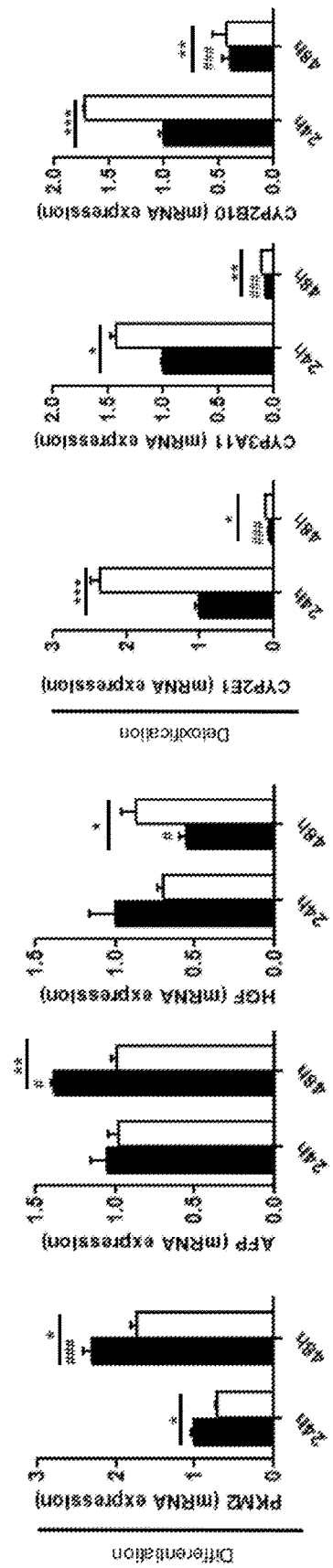
Fig. 2A
Fig. 2B
Fig. 2C
Fig. 2D

Fig. 3A
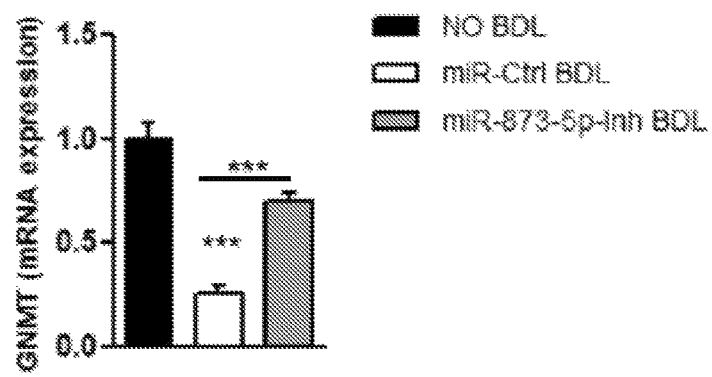
Fig. 3B
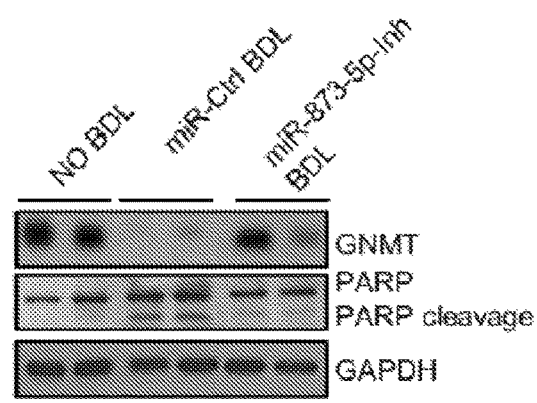
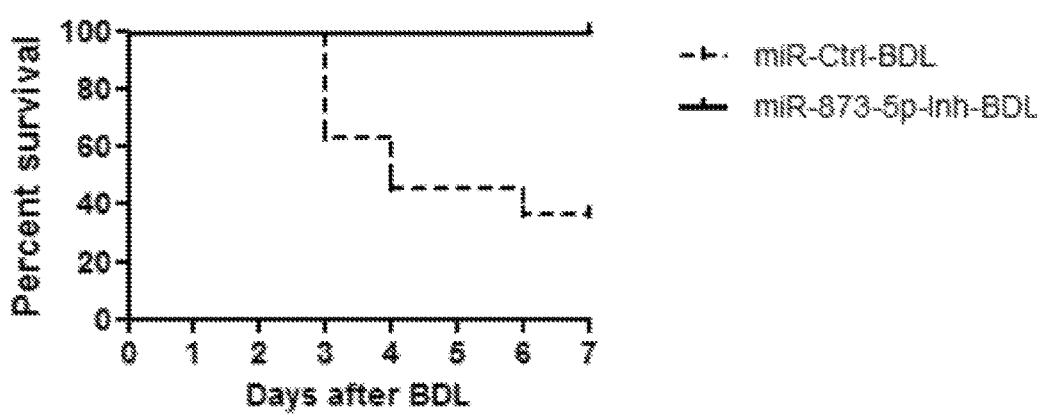
Fig. 3C

| Fold increase vs normal healthy liver | BCLC1 | BCLC2 | BCLC3 | BCLC4 | BCLC5 | BCLC6 | BCLC9 |
|---|---|---|---|---|---|---|---|
| hsa-miR-873 | 0,0 | >1000 | >1000 | 57,5 | 368,3 | 274,7 | 46,9 |
| hsa-miR-485-5p | 0,0 | 0,0 | 0,0 | 0,0 | 0,0 | 0,0 | 0,0 |
| hsa-miR-328 | 1,1 | 2,9 | 2,0 | 1,4 | 3,5 | 1,5 | 0,6 |
| hsa-miR-661 | 0,5 | 0,7 | 0,4 | 0,5 | 0,3 | 0,2 | 0,2 |
| hsa-miR-612 | 0,0 | 0,0 | 0,0 | 0,0 | 0,0 | 0,0 | 0,0 |
| hsa-miR-518d-5p | >1000 | >1000 | >1000 | >1000 | >1000 | >1000 | 0,0 |
| hsa-miR-920 | 0,0 | 0,0 | >1000 | 0,0 | 0,0 | >1000 | 0,0 |

Fig. 6A

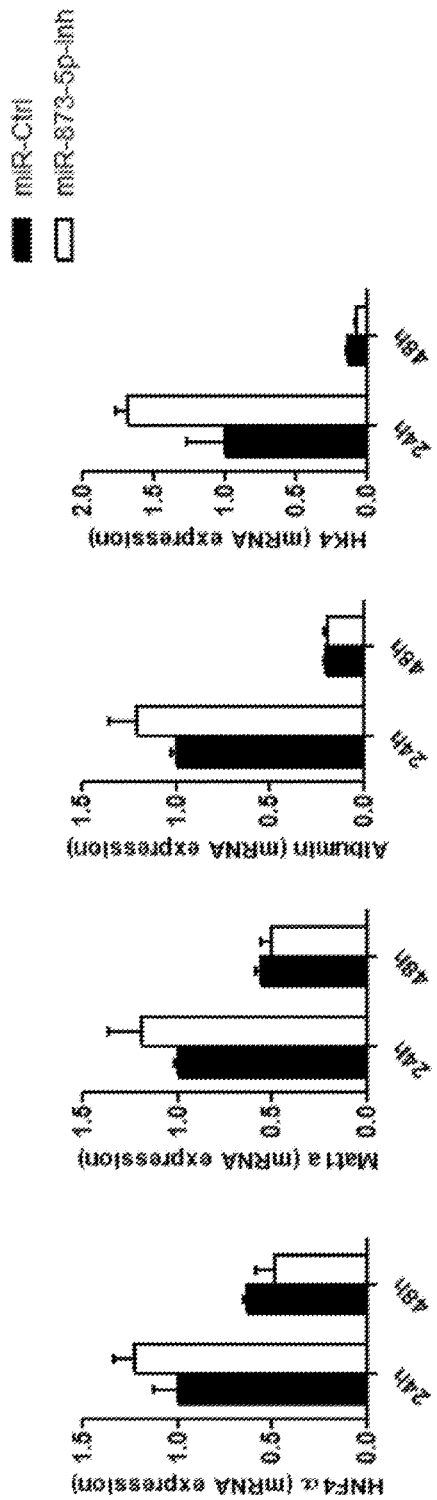
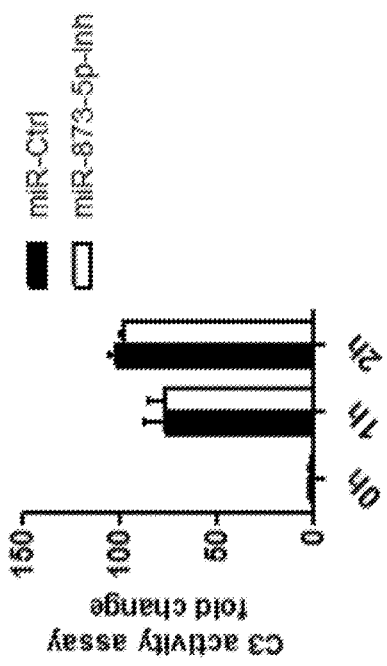
Fig. 7A
Fig. 7B ial application Ser. No. 62/207,456 filed Aug. 20, 2015, the disclosure of which is incorporated by reference herein in its entirety.

METHODS AND COMPOSITIONS TO TREAT LIVER DISEASES AND CONDITIONS

RELATED APPLICATIONS

This application is a National Stage Filing under U.S.C. § 371 of PCT International Application PCT/IB2016/001275, filed Aug. 20, 2016, which claims benefit under 35 U.S.C. § 119(e) of U.S. Provisional application Ser. No. 62/207,456 filed Aug. 20, 2015, the disclosure of which is incorporated by reference herein in its entirety.

FIELD OF THE INVENTION

The invention relates, in part, to methods and compounds that are useful to treat diseases and conditions such as those that impact the liver.

BACKGROUND

Hepatology is a field in continuous evolution: the epidemiology of chronic liver disease is changing at extremely high speed, with Non-Alcoholic Fatty Liver disease (NAFLD) taking over a position previously occupied by viral hepatitis and challenging cardiovascular disease as an increasing cause of metabolic syndrome related mortality. NAFLD is a clinical pathological term that encompass a wide range of pathological conditions ranging from accumulation of fat (fatty liver) to various degrees of inflammation and fibrosis, non-alcoholic steatohepatitis (NASH), and finally to cryptogenic cirrhosis and its clinical sequelae (hepatocelullar carcinoma, liver decompensation). Research and intervention have dramatically impacted hepatitis and cardiovascular disease, but there remains insufficient understanding of mechanisms involved in the progression of NAFLD to cirrhosis and cancer.

SUMMARY OF THE INVENTION

According to one aspect of the invention, methods for treating liver diseases and conditions in cells and/or a subject are provided. Methods of the invention, in some aspects may include administering to a cell and/or subject in need of such treatment an inhibitor of one or more microRNA compounds in an amount effective to treat the liver disease or condition in the cell and/or subject, respectively.

According to one aspect of the invention, methods for treating a liver disease or condition in a subject are provided. The methods include administering to a subject in need of such treatment a microRNA-inhibitor compound in an amount effective to treat the liver disease or condition in the subject. In some embodiments, the microRNA inhibitor compound decreases a microRNA activity in at least one cell in the subject. In certain embodiments, decreasing the microRNA activity includes decreasing a microRNA level or function. In some embodiments, the microRNA-inhibitor compound decreases microRNA activity and increases glycine N-methyltransferase (GNMT) enzyme activity in at least one cell in the subject. In some embodiments, the liver disease or condition is one or more of a liver cancer, a metastatic cancer in the liver, a precancerous liver condition, hepatocellular carcinoma, cirrhosis, a post-cancer liver condition, non-alcoholic fatty liver disease (NAFLD), accumulation of fat (fatty liver), liver inflammation, liver fibrosis, non-alcoholic steatohepatitis (NASH), cryptogenic cirrhosis and its clinical sequelae (hepatocelullar carcinoma, liver decompensation), steatohepatitis, and chemoresistance. In certain embodiments, treating the liver disease or condition includes increasing a GNMT activity in at least one cell in the subject, compared to a control level of the GNMT activity. In some embodiments, the microRNA-inhibitor compound is administered in a pharmaceutical composition, and optionally the pharmaceutical composition additionally includes a pharmaceutically acceptable carrier. In certain embodiments, the microRNA-inhibitor compound also includes one or more of a detectable label and a targeting agent. In some embodiments, the targeting agent is a liver-targeting agent. In some embodiments, the microRNA-inhibitor compound includes one or more of an RNA molecule, an miRNA sponge compound, an antisense inhibitor molecule, and a variant miRNA molecule. In certain embodiments, the microRNA-inhibitor compound includes a microRNA hairpin inhibitor molecule. In some embodiments, the microRNA-inhibitor compound inhibits at least one of miRNA-873-5p and miRNA-518d-5p. In certain embodiments, the liver disease or condition is not cancer. In certain embodiments, the method also includes administering to the subject one or more additional therapies for treatment of a liver cancer, a metastatic cancer in the liver, a precancerous liver condition, hepatocellular carcinoma, cirrhosis, a post-cancer liver condition, liver fibrosis, non-alcoholic fatty liver disease (NAFLD), accumulation of fat (fatty liver), liver inflammation, liver fibrosis, non-alcoholic steatohepatitis (NASH), cryptogenic cirrhosis, hepatocelullar carcinoma, liver decompensation, steatohepatitis, or chemoresistance. In some embodiments, the one or more additional therapies are administered to the subject at one or more of a time before, coincident with, and after administration of the miRNA-inhibitor compound to the subject. In some embodiments, the one or more additional therapies are independently selected from a radiation therapy, a surgical therapy, a chemotherapy, a molecular-targeted therapy, a cytostatic therapy, and a cytotoxic therapy. In certain embodiments, administering the miRNA-inhibitor compound and the one or more additional therapy, results in a synergistic treatment effect on the liver disease or condition in the subject. In some embodiments, the miRNA-inhibitor compound is an exogenous miRNA-inhibitor compound. In some embodiments, an administration means for the miRNA-inhibitor compound includes one or more of oral administration, subcutaneous administration, intravenous administration, intramuscular administration, intrahepatic administration, nasal administration, topical administration, transdermal administration, implant administration, and infusion administration. In certain embodiments, an administration formulation for the miRNA-inhibitor compound includes one or more of a slow release formulation, a nanoparticle, a microparticle, a hydrogel, an absorbable carrier, an implantable formulation, and a biodegradable matrix. In some embodiments, the administered miRNA-inhibitor compound reduces de-differentiation of at least one cell in the subject. In some embodiments, the at least one cell is a liver cell. In some embodiments, the subject is a mammal. In certain embodiments, the subject is a human.

According to another aspect of the invention, methods of increasing GNMT enzyme activity in a cell are provided. The methods include contacting the cell with an miRNA-inhibitor compound in an amount effective to increase GNMT enzyme activity in the cell and wherein the increase in GNMT enzyme activity reduces DNA hypermethylation in the cell. In certain embodiments, increasing the GNMT enzyme activity includes increasing a level or function of the GNMT enzyme in the cell. In some embodiments, the cell is an in vitro or an ex vivo cell. In some embodiments, the cell is an in vivo cell. In certain embodiments, the in vivo cell is in a subject and the contacting includes administering the miRNA-inhibitor compound to the subject. In some embodiments, the miRNA-inhibitor compound is administered in a pharmaceutical composition and optionally, the pharmaceutical composition additionally includes a pharmaceutically acceptable carrier. In some embodiments, the microRNA-inhibitor compound also includes one or more of a detectable label and a targeting agent, wherein optionally the targeting agent is a liver targeting agent. In certain embodiments, the microRNA-inhibitor compound includes one or more of an RNA molecule, an miRNA sponge compound, an antisense inhibitor compound, and a modified miRNA molecule. In some embodiments, the microRNA-inhibitor compound includes a microRNA hairpin inhibitor molecule. In some embodiments, the microRNA-inhibitor compound inhibits at least one of miRNA-873-5p and miRNA-518d-5p. In certain embodiments, the cell is a liver cell. In some embodiments, the cell is one or more of a liver cancer cell, a metastatic cancer cell, a precancerous liver cell, a cirrhotic liver cell, a post-cancer liver cell, a fibrotic liver cell, a hepatocyte, an inflammatory liver cancer cell, and a chemoresistant liver cell. In some embodiments, the cell is not a cancer cell. In certain embodiments, the method also includes contacting the cell with one or more additional therapies for treatment of a liver cancer, a metastatic cancer, a precancerous liver condition, hepatocellular carcinoma, cirrhosis, a post-cancer liver condition, non-alcoholic fatty liver disease (NAFLD), accumulation of fat (fatty liver), liver inflammation, liver fibrosis, non-alcoholic steatohepatitis (NASH), cryptogenic cirrhosis and its clinical sequelae such as hepatocelullar carcinoma, liver decompensation, steatohepatitis, or chemoresistance. In some embodiments, the cell is contacted with the one or more additional therapies at one or more of times before, coincident with, and after the cell is contacted with the miRNA-inhibitor compound. In some embodiments, the one or more additional therapies are independently selected from radiation therapy, surgery, chemotherapy, molecular targeted cancer therapy, cytostatic therapy, and cytotoxic therapy. In certain embodiments, contact with the miRNA-inhibitor compound and the one or more additional therapies results in a synergistic effect of the miRNA-inhibitor compound and/or the one or more additional therapies on the cell. In some embodiments, the miRNA-inhibitor compound is an exogenous miRNA-inhibitor compound. In some embodiments, the miRNA-inhibitor compound reduces de-differentiation of the contacted cell. In some embodiments, the subject is a mammal. In certain embodiments, the subject is a human.

According to another aspect of the invention, methods of decreasing GNMT enzyme activity in a cell are provided. The methods include contacting the cell with an miRNA-enhancer compound in an amount effective to decrease GNMT enzyme activity in the cell. In some embodiments, decreasing GNMT enzyme activity in the cell increases DNA hypermethylation in the cell. In certain embodiments, decreasing the GNMT enzyme activity includes decreasing a level or function of the GNMT enzyme in the cell. In some embodiments, the cell is an in vitro cell or an ex vivo cell. In some embodiments, the cell is an in vivo cell. In certain embodiments, the miRNA-enhancer compound is in a pharmaceutical composition and optionally, the pharmaceutical composition also includes a pharmaceutically acceptable carrier. In some embodiments, the microRNA-enhancer compound also includes one or more of a detectable label and a targeting agent. In some embodiments, the microRNA-enhancer compound includes a microRNA sequence. In certain embodiments, the microRNA-enhancer compound includes at least one of miRNA-873-5p and miRNA-518d-5p, or a functional variant thereof. In certain embodiments, the administered miRNA-enhancer compound increases de-differentiation of the contacted cell. In some embodiments, the contacted cell is a liver cell.

According to another aspect of the invention, methods of identifying an miRNA-modulating compound that alters an activity of one or both of miRNA-873-5p and miRNA-518d-5p in a cell are provided. The methods include, (a) contacting a cell a candidate miRNA-modulating compound; (b) determining the amount of activity of one or both of miRNA-873-5p and miRNA-518d-5p in the cell; and (c) comparing the amount of activity determined for one or both of miRNA-873-5p and miRNA-518d-5p with a control amount of activity of miRNA-873-5p and miRNA-518d-5p, respectively, wherein a decrease in the amount of activity of one or both of miRNA-873-5p and miRNA-518d-5p in the contacted cell compared to the control amount of activity of miRNA-873-5p and miRNA-518d-5p, respectively identifies the candidate miRNA-modulating compound as an miRNA-inhibiting compound and wherein an increase in the amount of activity of one or both of miRNA-873-5p and miRNA-518d-5p in the contacted cell compared to the control amount of activity of miRNA-873-5p and miRNA-518d-5p, respectively identifies the candidate miRNA-modulating compound as an miRNA-enhancing compound. In some embodiments, determining the amount of activity of one or both of miRNA-873-5p and miRNA-518d-5p in the cell includes comparing GNMT enzyme activity in the contacted cell to GNMT activity in a control cell not contacted with the candidate miRNA-modulator compound, wherein an increase in GNMT enzyme activity in the contacted cell versus the control cell identifies the candidate miRNA-modulator as an miRNA-inhibitor compound and wherein a decrease in GNMT enzyme activity in the contacted cell versus the control cell identifies the candidate miRNA-modulator as an miRNA-enhancer compound. In certain embodiments, the cell is an in vitro cell or an ex vivo cell. In some embodiments, the cell is an in vivo cell. In some embodiments, the contacted cell is a liver cell. In certain embodiments, the contacted cell is one or more of a liver cancer cell, a metastatic cancer cell, a precancerous liver cell, a cirrhotic liver cell, a post-cancer liver cell, a fibrotic liver cell, a hepatocyte, an inflammatory liver cancer cell, a chemoresistant liver cell, and a normal cell. In some embodiments, the method also includes administering the identified miRNA-inhibiting compound to a subject pharmaceutical composition ct. In some embodiments, the subject has a liver disease or condition. In some embodiments, the subject is a mammal. In certain embodiments, the subject is a human.

According to another aspect of the invention, pharmaceutical compositions for treating a liver disease or condition in a subject are provided, the pharmaceutical compositions including at least one miRNA-modulating compound in an amount effective to treat the liver disease or condition in the subject. In some embodiments, the miRNA-modulating compound is an miRNA-activity-inhibiting compound. In certain embodiments, the miRNA-inhibiting compound inhibits activity of at least one of miRNA-873-5p and miRNA-518d-5p in the subject. In some embodiments, inhibiting the miRNA activity comprises decreasing the level or function of the miRNA. In some embodiments, the microRNA-inhibitor compound comprises one or more of an RNA molecule, an miRNA sponge compound, an antisense inhibitor molecule, and a variant miRNA molecule. In certain embodiments, the microRNA-inhibitor compound comprises a microRNA hairpin inhibitor molecule. In some embodiments, the microRNA-inhibitor compound inhibits at least one of miRNA-873-5p and miRNA-518d-5p. In some embodiments, the liver disease or condition is: liver cancer, a metastatic cancer in the liver, a precancerous liver condition, hepatocellular carcinoma, cirrhosis, a post-cancer liver condition, non-alcoholic fatty liver disease (NAFLD), fatty liver, liver inflammation, liver fibrosis, non-alcoholic steatohepatitis (NASH), cryptogenic cirrhosis, hepatocelullar carcinoma, liver decompensation, steatohepatitis, or chemoresistance. In certain embodiments, the miRNA-modulating compound is an miRNA-activity-enhancing compound and wherein enhancing the miRNA activity comprises increasing the level or function of the miRNA the subject. In some embodiments, the pharmaceutical composition further comprises a pharmaceutically acceptable carrier. In certain embodiments, the pharmaceutical composition further comprises a targeting agent. In some embodiments, at least one of: the liver disease or condition is not cancer and the subject does not have cancer. In some embodiments, the subject is a mammal. In certain embodiments, the subject is a human.

The present invention is not intended to be limited to a composition or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE SEQUENCES

SEQ ID NO: 1 Homo sapiens sequence for MIR-873-5p referred to as: hsa-miR-873-5p:
gcaggaacuugugagucuccu, which has miRBase Accession number: MIMAT0004953.

SEQ ID NO: 2 Mus musculus sequence for MIR-873-5p referred to as: mmu-miR-873a-5p:
gcaggaacuugugagucuccu.

SEQ ID NO: 3 Rattus novergicus sequence for MIR-873-5p referred to as: rno-miR-873-5p:
gcaggaacuugugagucuccu.

SEQ ID NO: 4 Populus trichocarpa sequence for MIR-873-5p referred to as: ptr-miR-873:
gcaggaacuugugagucuccu.

SEQ ID NO: 5 Bos taurus sequence for MIR-873-5p referred to as: bta-miR-873:
gcaggaacuugugagucuccu.

SEQ ID NO: 6 Equus caballus sequence for MIR-873-5p referred to as: eca-miR-873:
gcaggaacuugugagucuccu.

SEQ ID NO: 7 Pongo pygmaeus sequence for MIR-873-5p referred to as: ppy-miR-873:
gcaggaacuugugagucuccu.

SEQ ID NO: 8 Homo sapiens sequence for MIR-518d-5p referred to as: hsa-miRNA-518d-5p:
cucuagagggaagcacuuucug, which has miRBase Accession number: MIMAT0005456.

SEQ ID NO: 9 Homo Sapiens sequence for MIR-526a referred to as hsa-miR-526a:
cucuagagggaagcacuuucug.

SEQ ID NO: 10 Homo Sapiens sequence for MIR-520c-5p referred to as hsa-miR-520c-5p:
cucuagagggaagcacuuucug.

SEQ ID NO: 11 Populus trichocarpa sequence for MIR-526a referred to as ptr-miR-526a:
cucuagagggaagcacuuucug.

SEQ ID NO: 12 Gorilla gorilla sequence for MIR-518d-5p referred to as ggo-miRNA-518d-5p:
cucuagagggaagcacuuucug.

SEQ ID NO: 13 Gorilla gorilla sequence for MIR-520C referred to as: ggo-miR-520cd:
cucuagagggaagcacuuucug.

SEQ ID NO: 14 Gorilla gorilla sequence for MIR-526a referred to as ggo-miR-526a:
cucuagagggaagcacuuucug.

SEQ ID NO: 15 Pongo pygmaeus sequence for MIR-518g-5p referred to as ppy-miRNA-518g-5p: cucuagagggaagcacuuucug.

BRIEF DESCRIPTION OF THE DRAWINGS

FIG. 1A-F shows graphs of results indicating that miR-873-5p targets GNMT expression in the liver. FIG. 1A shows two graphs of results from a correlation study between miR-873-5p and GNMT expression levels in liver tumors (left graph) and in cohort of cirrhotic patients (right graph). FIG. 1B shows results of qPCR analysis of GNMT (left graph) and miR-873-5p (Right graph) in 1 day postnatal and adult mice liver. FIG. 1C shows results of qPCR analysis of GNMT (left graph) and miR-873-5p in hepatocytes in culture at different time points. FIG. 1D shows results of qPCR analysis of GNMT (left graph) and miR-873-5p at different time points of BDL. FIG. 1E shows results of qPCR analysis of GNMT (left graph) and miR-873-5p under deoxycholic acid treatment of primary hepatocytes. FIG. 1F shows results of luciferase reporter assay of GNMT expression in hepatocytes after miR-873-5p overexpression (left graph) and in BCLC3 liver cancer cells (right graph) after miR-873-5p inhibition. Statistical analysis represented: $p<0.05*$; $p<0.01$; $p<0.001*$.

FIG. 2A-D provides graphs of results demonstrating that miR-873-5p inhibition prevents hepatocytes from de-differentiation. Graphs show results from analysis performed on the indicated genes' mRNA expression by qPCR in control and miR-873-5p-inhibited hepatocytes in culture at different time points of de-differentiation. FIG. 2A shows results for GNMT. FIG. 2B shows results for HNF4a (left), albumin (center), and HK4 (right). FIG. 2C shows results for PKM2 (left), AFP (center), and HGF (right). FIG. 2D shows results for CYP2E1 (left), CYP3A11 (center), and CYP2B10 (right). Statistical analysis represented: $p<0.05*$; $p<0.01$; $p<0.001*$. # compares 24 h to 48 h (miR-Ctrl). Black bars represent miR-Ctl treated and white bars represent miR-873-5p-inh treated.

FIG. 3A-F shows graphs, blots, and photomicrographic images of results demonstrating that miR-873-5p inhibition after bile duct ligation in mice regressed fibrotic phenotype. FIG. 3A is a graph and a Western blot showing GNMT expression measured by mRNA and protein levels. FIG. 3B shows an apoptosis analysis mediated by PARP cleavage. FIG. 3C is a Kaplan Meier curve depicting survival in mice under miR-Ctrl and miR-873-5p-inhibited mice after BDL. FIG. 3D shows results of analysis of Caspase 3 (C3) activity levels under miR-Ctrl and miR-873-5p-inhibited mice at 7 days of BDL. FIG. 3E shows results of analysis of transaminases (ALT and AST) levels under miR-Ctrl and miR-873-5p-inhibited mice at 7 days of BDL. FIG. 3F shows photomicrographic images of Sirius Red, F4/80, αSMA and CK19 staining in liver sections from miR-Ctrl and miR-873-5p-inhibited mice at 7 days of BDL, and provides corresponding graphs of changes in control versus miR-873-5p inhibited BDL. (Values are mean±SEM. *P<0.05, **P<0.01, [Control vs. 873-Inh]).

FIGS. 4A-C show results of analysis of the indicated genes by qPCR in control and miR-873-5p-inhibited mice. FIG. 4A shows results for TGFβ (left) and MMP9 (right). FIG. 4B shows results for FXR, HNF1α, Abcg5, and Abcg8HGF (left to right). FIG. 4C shows results for iNOS (left), SAA1 (center), and CXCL1 (right), top row and TNFα (left) and IL-6 (right), bottom row. (Values are mean±SEM. *P<0.05, **P<0.01, [Control vs. 873-5p-Inh]). Black bars represent NO BDL, white bars represent miR-Ctrl BDL, and grey bars represent miR-837-5p-inh BDL.

FIG. 5A is a graph of Caspase 3 (C3) activity in control and miR-873-5p-inhibited hepatocytes before and after 2 h of DCA treatment (100 μM). FIGS. 5B-D provide graphs of results from mRNA expression analysis of the indicated genes by qPCR in control and inhibited miR-873-5p hepatocytes at different time points of DCA treatment. FIG. 5B shows results for GNMT, Bcl-2, HNF1α, and HNF4a (left to right). FIG. 5C shows results for FXR, SHP, BSEP, Abcg5 and Abcg8, (top row, left to right), and MRP1, MRP2, MRP3, MRP4, and MRP5 (bottom row, left to right). FIG. 5D shows results for mdr1, mdr2, and mdr3 (left to right). Statistical analysis represented: p<0.05*; p<0.01; p<0.001* (Control (ctl) vs. 873-5p-Inh). Black bars represent miR-Ctl and white bars represent miR-837-5p-inh treatment.

FIG. 6A-C provides information relating to miR-873-5p and miRNA-518d-5p expression in the liver. FIG. 6A is a table of results of expression analysis of indicated miRNAs in tumoral liver samples compared to healthy liver. FIG. 6B is a graph showing results of a correlation study between miRNA-518d-5p and GNMT expression levels in liver tumors. FIG. 6C is a schematic drawing showing putative binding site of miR-873-5p in a GNMT 3'UTR fragment.

FIG. 7A-B shows graphs demonstrating a lack of effect of miR-873-5p-inhibition in the absence of GNMT. FIG. 7A provides graphs of results of analysis of indicated genes' mRNA expression by qPCR in control and miR-873-5p-inhibited Gnmt-KO-hepatocytes in culture at different time points of de-differentiation, showing results for HNH4α, Mat1a, Albumin, and HK4 (left to right). FIG. 7B is a graph showing Caspase 3 activity assay in control and miR-873-5p-inhibited hepatocytes derived from the Gnmt-KO mice after 1 h and 2 h of DCA treatment (100 μM). Statistical analysis represented: p<0.05*; p<0.01**; # compares to 0 h DCA miR-Ctrl.

FIG. 9A shows GNMT expression in the liver of healthy (control), steatotic, and NASH patients. FIG. 9B shows miR-873-5p expression in the liver of healthy (control), steatotic, and NASH patients.

FIG. 9C shows the correlation between GNMT and miR-873-5p expression in the liver of healthy and NASH patients. FIG. 9D shows the level of miR-873-5p in the serum of healthy and NAFLD/NASH patients.

FIGS. 10A-C shows results from mice fed normal diet (Chow) compared to mice fed a methionine and choline deficient diet (MCDD) in FIG. 10A, mice fed high fat diet (HFD) in FIG. 10B, and mice fed high cholesterol (HC) diet in FIG. 10C. Each mouse subject was fed the indicated diet over a period of four weeks, and then miR-873-5p and GNMT mRNA levels were determined.

FIG. 11A shows schematic diagram of mouse injection. FIG. 11B-C show results of histological analysis including Hematoxilin and Eosin (H&E), Sudan III, Sirius red, F4/80, SMA, and GNMT in the liver of anti-miR treated or normal control (ctrl) mice. FIG. 11D-F provides three graphs showing serum levels of hepatic transaminases (FIG. 11D), triglycerides (FIG. 11E), and ketone bodies (FIG. 11F). FIG. 11G provides a graph showing hepatic free fatty acids, triglycerides and cholesterol of mice fed with standard (Chow) and MCD diet and treated or not with anti-miR-873-5p. The MCD diet is also referenced herein interchangeably as MCDD and DDMC.

DETAILED DESCRIPTION

Figure 1A:
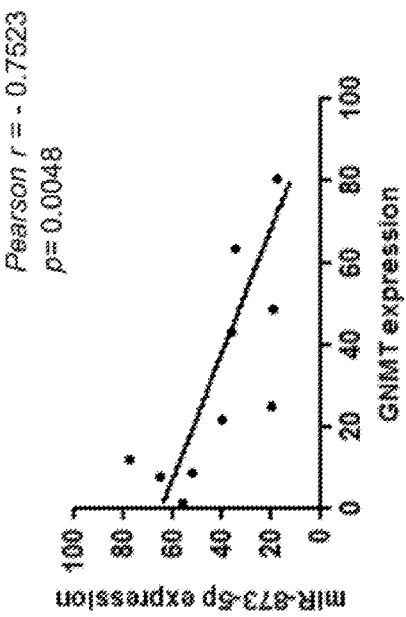

It has now been identified that miRNA-873-5p and miRNA-518d-5p both impact liver disease (non-limiting examples of which include: NAFLD, NASH, liver inflammation, fatty liver, liver decompensation, liver fibrosis, cirrhosis, etc.), and liver cancer development and treatment through regulation of GNMT expression. It has also been discovered that high levels of miRNA-873-5p and miRNA-518d-5p are associated with low levels of GNMT in liver disease animal models, and are also present in subjects having certain liver diseases or conditions. The invention, in some aspects includes inhibiting activity of one or both of miRNA-873-5p and miRNA-518d-5p as treatment of liver pro-oncogenic conditions (LPOC), such as NAFLD, cirrhosis, as well as hepatocellular carcinoma (HCC) and other liver diseases and conditions. In certain aspects of the invention, inhibition of an activity of one or both of miRNA-873-5p and miRNA-518d-5p may increase chemoprotection in LPOC and reduce antitumor chemoresistance in diseases associated with activity of miRNA-873-5p and miRNA-518d-5p. In certain aspects of the invention methods are provided that include targeted reduction of miRNA-873-5p and/or miRNA-518d-5p activity levels as treatment for NAFLD, cirrhosis, HCC, liver pro-oncogenic conditions, and other liver diseases and conditions.

MicroRNAs (also referred to herein as miRNAs) are small endogenous RNA molecules that act to direct the RNA induced silencing complex (RISC), to target sequences in mRNA molecules, RISC-loaded miRNAs bind in a sequence-specific way to their target mRNAs, and repress the target mRNAs through means such as translational inhibition and RNA destabilization, Sequences of microRNAs set forth herein as SEQ ID NOs: 1-15 include: *Homo*

*sapiens* sequence for MIR-873-5p also referred to as: hsa-miR-873-5p, which has an identical sequence to the *Mus musculus* sequence for MIR-873-5p also referred to as: mmu-miR-873a-5p, the *Rattus novergicus* sequence for MIR-873-5p also referred to as: rno-miR-873-5p, the *Populus trichocarpa* sequence for MIR-873-5p also referred to as: ptr-miR-873, the *Bos taurus* sequence for MIR-873-5p also referred to as: bta-miR-873, the *Equus caballus* sequence for MIR-873-5p also referred to as: eca-miR-873, and the *Pongo pygmaeus* sequence for MIR-873-5p also referred to as: ppy-miR-873. The *Homo sapiens* sequence for MIR-518d-5p also referred to as: hsa-miRNA-518d-5p is also provided and has an identical sequence to the MIR-526a also referred to as hsa-miR-526a, the *Homo sapiens* sequence for MIR-520c-5p also referred to as hsa-miR-520c-5p, the *Populus trichocarpa* sequence for MIR-526a also referred to as ptr-miR-526a, the Gorilla gorilla sequence for MIR-518d-5p also referred to as ggo-miRNA-518d-5p, the Gorilla gorilla sequence for MIR-520C also referred to as: ggo-miR-520cd, the Gorilla gorilla sequence for MIR-526a also referred to as ggo-miR-526a, and the *Pongo pygmaeus* sequence for MIR-518g-5p also referred to as ppy-miRNA-518g-5p.

As used herein, inhibition of microRNA activity means repression of the microRNA's target mRNA and reduction of protein transcribed from the target mRNA. As used herein, enhancement of microRNA activity means the heightening of the effect of the microRNA's target mRNA and increase of the amount of protein transcribe from the target miRNA, It now has been determined that the activity of the microRNAs: miRNA-873-5p and miRNA-518d-5p in cells and subjects correlates with the presence or absence of diseases and conditions, including but not limited to liver diseases and conditions. A higher level of miRNA-873-5p and miRNA-518d-5p activity in one or more of a cell, tissue, or organ increases the likelihood of a liver disease or condition in the cell, tissue, or organ, respectively. A decreased level of miRNA-873-5p and miRNA-518d-5p activity in one or more of a cell, tissue, or organ decreases the likelihood of a liver disease or condition in the cell, tissue, or organ, respectively.

It has also now been identified that increasing activity of miRNA-873-5p and miRNA-518d-5p in a cell may result in de-differentiation of the cell, and may result in acquisition of more "fetal" characteristics by the cell. Certain aspects of the invention include enhancing the activity of one or both of miRNA-873-5p and miRNA-518d-5p in a cell, tissue, organ, or subject.

miRNA-873-5p, miRNA-518d-5p, and GNMT Activity.

The invention in some aspects relates to methods for modulating one or more of miRNA-873-5p, miRNA-518d-5p, and GNMT activity in a cell, tissue, and/or subject. As used herein the term "modulating" means changing a level of an miRNA-873-5p, miRNA-518d-5p, and/or GNMT activity (e.g., level and/or function) in a cell. In some embodiments of the invention, changing miRNA-873-5p, miRNA-518d-5p, and/or GNMT activity includes changing a level of one or more of miRNA-873-5p, miRNA-518d-5p, and GNMT in a cell or tissue. Thus, decreasing activity of one or both of miRNA-873-5p and miRNA-518d-5p in a cell may include decreasing the level (e.g., amount) of one or both of miRNA-873-5p and miRNA-518d-5p in the cell.

Some embodiments of the invention include methods of administering one or more of an miRNA-873-5p-inhibitor compound and an miRNA-518d-5p-inhibitor compound to a cell, tissue or subject in an amount effective to decrease one or more of miRNA-873-5p and miRNA-518d-5p activity in the cell, tissue, or subject as a treatment for the liver disease or condition. A liver disease or condition such as liver cancer, a metastatic cancer in the liver, a precancerous liver condition, hepatocellular carcinoma, cirrhosis, a post-cancer liver condition, non-alcoholic fatty liver disease (NAFLD), fatty liver, liver inflammation, liver fibrosis, non-alcoholic steatohepatitis (NASH), cryptogenic cirrhosis, hepatocelullar carcinoma, liver decompensation, steatohepatitis, and chemoresistance may be treated in a cell or tissue contacting the cell or tissue with one or both of an miRNA-873-5p-inhibitor compound and an miRNA-518d-5p-inhibitor compound thereby decreasing activity of miRNA-873-5p and miRNA-518d-5p, respectively, in the cell or tissue, thus treating the liver disease or condition in the cell or tissue.

A liver disease or condition such as liver cancer, a metastatic cancer in the liver, a pro-oncogenic liver condition, a precancerous liver condition, hepatocellular carcinoma, cirrhosis, a post-cancer liver condition, non-alcoholic fatty liver disease (NAFLD), fatty liver, liver inflammation, liver fibrosis, non-alcoholic steatohepatitis (NASH), cryptogenic cirrhosis, hepatocelullar carcinoma, liver decompensation, steatohepatitis, and chemoresistance may be treated in a subject by administering one or more of an miRNA-873-5p-inhibitor compound and an miRNA-518d-5p-inhibitor compound to the subject in an effective amount to decrease activity of miRNA-873-5p and miRNA-518d-5p, respectively, in the subject, to treat the liver disease or condition in the subject.

In some embodiments, methods of the invention include decreasing activity of one or more of miRNA-873-5p and miRNA-518d-5p in a cell, tissue, or subject, for example, by delivering a microRNA-inhibitor compound into the cell, tissue or subject, to treat a liver disease or condition. To treat a liver disease or condition in a subject, one or more cells may be contacted with a microRNA-inhibitor compound, such as an miRNA-873-5p-inhibitor compound or an miRNA-518d-5p-inhibitor compound, which results in a decreased level of activity of at least one of miRNA-873-5p and miRNA-518d-5p in the cell. If the cell to be contacted with the microRNA-inhibiting compound is in a subject, the microRNA-inhibiting compound can be administered to the subject.

MicroRNA Inhibitor Compounds and Enhancer Compounds

Examples of microRNA-inhibitor compounds useful in some embodiments of methods of the invention include, but are not limited to miRNA-873-5p-inhibitor compounds and miRNA-518d-5p-inhibitor compounds. Non-limiting examples of a microRNA-enhancer compound that may be useful in certain embodiments of methods of the invention to increase activity of miRNA-873-5p or miRNA-518d-5p are exogenous double-stranded miRNA mimic compounds, such as a miRNA-873-5p mimic compound or a miRNA-518d-5p mimic compound. The invention in part, relates to methods of modulating microRNA activity. In some instances modulating is "inhibiting" microRNA activity and in other instances modulating is "enhancing" microRNA activity, thus the terms "microRNA-inhibitor" compound and "microRNA-enhancer" compound may be referred to herein by the collective term "microRNA-modulator" compound. A skilled artisan will recognize that as used herein, terms such as higher, lower, decreased, inhibited, reduced, increased, and enhanced may represent relative levels or values as compared to control levels or values.

Methods to Reduce miRNA-873-5p and/or miRNA-518d-5p Activity

The invention, in part, includes methods of reducing activity (e.g., levels and/or function) of one or more of the microRNAs miRNA-873-5p and miRNA-518d-5p to treat a liver disease or condition in a cell, tissue, organ, and/or subject. Compositions, compounds, and methods of the invention may be used to treat a subject having, or at risk of having a liver disease or condition that may be characterized and/or associated with an activity of miRNA-873-5p and/or miRNA-518d-5p in one or more of a cell, tissue, or subject that increases the likelihood of a liver disease or condition in the cell, tissue, or subject, respectively. Certain aspects of the invention provide methods and compounds that may be used to inhibit activity of miRNA-873-5p and/or miRNA-518d-5p in a cell, which increases glycine N-methyltransferase (GNMT) enzyme activity in the cell. In some embodiments, methods of the invention include contacting a cell with an miRNA-inhibitor compound in an amount that is effective to increase GNMT enzyme activity in the cell. In some embodiments, methods of the invention include contacting a cell with an miRNA-inhibitor compound in an amount that is effective to reduce DNA hypermethylation in the cell to treat liver diseases or conditions in cells, tissues, organs, and subjects. The invention in part, also relates to decreasing/inhibiting miRNA-873-5p and miRNA-518d-5p activity from an initial activity level in one or more cells in a subject to a lower level of activity that is effective to reduce or eliminate symptoms of and to treat a liver disease or condition in the subject.

In certain embodiments of the invention, inhibiting miRNA-873-5p and/or miRNA-518d-5p activity includes reducing the function of miRNA-873-5p and/or miRNA-518d-5p in a cell, tissue, and/or subject. Reducing miRNA-873-5p and/or miRNA-518d-5p function may result from a decrease in the amount of miRNA-873-5p and/or miRNA-518d-5p and/or from a decrease in activity of the miRNA-873-5p and/or miRNA-518d-5p molecule in a cell, tissue, or subject. It will be understood that in some embodiments, methods of the invention reduce the activity of an miRNA-873-5p and/or miRNA-518d-5p without altering the amount of the miRNA-873-5p and/or miRNA-518d-5p in a cell or tissue. A non-limiting example of a method of the invention to reduce the activity of an miRNA-873-5p and/or miRNA-518d-5p includes contacting the miRNA-873-5p or miRNA-518d-5p with a microRNA inhibitor that binds to miRNA-873-5p or miRNA-518d-5p and inhibits the activity of the miRNA-873-5p or miRNA-518d-5p, respectively. It will be understood that in some embodiments, methods of the invention reduce the amount of miRNA-873-5p and/or miRNA-518d-5p in a cell or tissue, thereby reducing miRNA-873-5p and/or miRNA-518d-5p activity in the cell, tissue, or subject. Treatment methods of the invention may include administering one or more microRNA inhibitor compounds to a cell, tissue, or subject to reduce an activity of miRNA-873-5p and/or miRNA-518d-5p, to reduce an amount of miRNA-873-5p and/or miRNA-518d-5p, and/or to reduce both the amount and activity of miRNA-873-5p and/or miRNA-518d-5p in the cell, tissue, and/or subject.

Molecules and compounds that inhibit an miRNA-873-5p and/or an miRNA-518d-5p activity are referred to herein as microRNA-inhibitor compounds. A microRNA-inhibitor compound decreases the ability of a target miRNA to act on the miRNA's target mRNA. As used herein the term "target miRNA" means the miRNA whose activity is to be reduced by the miRNA-inhibitor compound. In certain aspects of the invention the target microRNA is miRNA-873-5p. In some aspects of the invention the target microRNA is miRNA-518d-5p.

Reduction in activity of a target miRNA by administration of a microRNA inhibitor compound may result from direct or indirect inhibition of its target microRNA's activity. As used herein, the term "direct inhibition" means microRNA activity inhibition that results from binding of a microRNA-inhibitor compound to its target microRNA. In some embodiments of the invention, direct microRNA inhibition reduces or eliminates binding of the target microRNA to its target mRNA, thereby inhibiting the target microRNA's activity. In certain embodiments of the invention, direct microRNA inhibition may not prevent binding of a microRNA to its target mRNA, but may interfere with the interaction between the microRNA and its target mRNA, thereby inhibiting the microRNA's activity. As used herein, the term "indirect microRNA inhibition" means inhibition of microRNA activity that results from binding of a microRNA-inhibitor compound to a microRNA's target mRNA. In some embodiments of the invention, indirect microRNA inhibition results in a reduction or elimination of binding of the microRNA to its target mRNA, thereby inhibiting the microRNA's activity. In certain embodiments of the invention, indirect microRNA inhibition may not prevent binding of a microRNA to its target mRNA, but may interfere with the interaction between the microRNA and its target mRNA, thereby inhibiting the microRNA's activity. General methods to prepare and use microRNA-inhibitor compounds (both direct and indirect) are described in publications such as: U.S. Pat. Nos. 8,288,356; 8,906,871; 8,247,543; US Patent Application Publication No. US 2013-0171242; U.S. Pat. No. 9,096,850; and Robertson, B. et al., *Silence* 2010, 1:10 (doi:10.1186/1758-907X-1-10); Baigude, H. and Rana, T. M. 2014, Nanomedicine (Lond) 9:2545; Esau, C. C. 2008, Methods 44:55; and Zhao, J. J. et al., 2015 Cancer Res. Epub ahead of print; the content of each of which is incorporated by reference herein in its entirety.

Numerous types of microRNA-inhibitor compounds may be used in aspects of the invention, including, but not limited to compounds comprising one or more: RNA molecules, antagomirs, blockmirs, miRNA sponge molecules, antisense inhibitor molecules, variant miRNA molecules, etc. A non-limiting example of a microRNA-inhibitor compound that reduces activity of miRNA-873-5p is miRIDIAN microRNA Hairpin Inhibitor miRNA-873-5p (Dharmacon, Lafayette, Colo.), which is a single-stranded, chemically-enhanced RNA oligonucleotide that binds to and sequesters the complimentary, mature microRNA strand miRNA-873-5p. A non-limiting example of a microRNA-inhibitor compound that reduces activity of miRNA-518d-5p is miRIDIAN microRNA Hairpin Inhibitor miRNA-518d-5p (Dharmacon, Lafayette, Colo.), which is a single-stranded, chemically-enhanced RNA oligonucleotide that binds to and sequesters the complimentary, mature microRNA strand miRNA-518d-5p. Other sequences that bind to and reduce activity of miRNA-873-5p or miRNA-518d-5p include RNA oligonucleotides that comprise a sequence complementary to the sequence of miRNA-873-5p or miRNA-518d-5p, respectively. In some aspects of the invention an inhibitor compound is used in methods to inhibit another miRNA disclosed herein, for example, MIR-526a, MIR-520c-5p, MIR-520C, and MIR-518g-5p.

Additional types of molecules that may be used in compounds and methods of the invention to inhibit microRNA activity include, but are not limited to antagomirs, blockmirs, and microRNA sponges. Antagomirs are chemically modified oligonucleotides that bind specifically to a target microRNA of interest and inhibits activity of the cellular target of the microRNA. In certain aspects of the invention one or more of an antagomir that binds to and inhibits miRNA-873-5p and an antagomir that binds to and inhibits miRNA-518d-5p may be delivered to a cell to treat a liver disease or condition in the cell, and/or may be delivered to a subject to treat a liver disease or condition in the subject. Methods of to prepare and administer antagomirs are known in the art, see for example, Krütnzfeldt, J. et al., (2005) Nature 438 (7068): 685-9; Czech M. P. (2006) N. Engl. J. Med. 354 (11): 1194-5; Tay, F. C. et al., 2015, Adv Drug Deliv Rev. 81:117; Ebert, M. S. and Sharp, P. A. 2010, RNA 16:2043; and Velu C. X. 2014, J. Clin Invest. 124:222; each of which is incorporated herein by reference in its entirety.

Blockmirs are designed such that they include a sequence complementary to a target mRNA sequence that serves as a binding site for microRNA. Blockmirs bind to the mRNA and thereby inhibit microRNA activity by sterically blocking the microRNA from binding to the same site on the target mRNA, which prevents the degradation of the target mRNA via RNA-induced silencing complex (RISC). Methods of to prepare and administer blockmirs are known in the art, see for example, U.S. Pat. No. 8,691,965; Stenvang et al. Silence 2012, 3:1; and Young, J. A. 2013, Blood 122:2911; each of which is incorporated herein by reference in its entirety.

Sponge RNAs are small synthetic RN As that bind to multiple microRNAs that have the same sequence in their "seed region", Non-limiting examples of miRNA sponge compounds are highly expressed transgenes that comprise multiple miRNA target sites and thus can bind to and sequester miRNAs. The microRNA "sponge" administered to (e.g., delivered to or expressed in) a cell may result in continuous miRNA loss of function in the cell. Sponge RNAs useful in some embodiments of methods of the invention comprise RNA sequences that provide complementary binding sites to miRNA-873-5p or miRNA-518d-5p, and when expressed in or delivered to a cell, the sponge RNAs function within the cell to inhibit activity of miRNA-873-5p or miRNA-518d-5p, respectively. A microRNA sponge's binding sites may be complementary to and specific to the miRNA seed region of miRNA-873-5p or miRNA-518d-5p. In certain aspects of the invention the seed region of miRNA-873-5p may be nucleotides 2-8 of the miRNA-873-5p sequence. In certain aspects of the invention the seed region of miRNA-518d-5p may be nucleotides 2-8 of the miRNA-518d-5p sequence. The design and use of sponge RNAs is well known in the art. See for example Ebert, M., et al. Nature Methods 4, 721-726 (2007) and Ebert, M. & P. Sharp, R N A. 2010 November; 16(11): 2043-2050, each of which is incorporated herein by reference in its entirety.

Antisense inhibition methods and compounds may be used in aspects of the invention to reduce activity of miRNA-873-5p or miRNA-518d-5p and to increase GNMT activity. Non-limiting examples of antisense inhibitor molecules are: anti-miRNAs and chemically modified antisense oligonucleotides that sequester mature miRNA and thereby compete with cellular target mRNAs. The competition reduces the level of binding of the miRNA with its cellular target mRNA and thus inhibits the activity of the miRNA. Antisense inhibition compounds and methods are known in the art. See for example: A. G. Torres et al., RNA (2011), 17:933-943; and Torres A. G. 2011, Artif DNA PNA XNA 2:71; each of which is incorporated herein by reference in its entirety.

Variant miRNA compounds and may be used in some embodiments of the invention to reduce activity of miRNA-873-5p or miRNA-518d-5p and/or to increase GNMT activity. Non-limiting examples of variant miRNA molecules are "null" miRNAs that bind to their target but that binding does not result in miRNA activity. See for example: Katoh T. 2009 Genes Dev 23:433 and Wyman S. K. 2011 Genome Res 21:1450; each of which is incorporated herein by reference in its entirety.

Method and Compounds to Increase miRNA-873-5p and/or miRNA-518d-5p Activity

The invention, in part, includes methods of increasing activity (e.g., levels and/or function) of one or more of the microRNAs miRNA-873-5p and miRNA-518d-5p. Increasing such activity may result in de-differentiation of a treated cell and a treated cell may acquire "fetal" cell characteristics. Compositions, compounds, and methods of the invention may be used to contact (e.g., treat) one or more cells in order to increase miRNA-873-5p and miRNA-518d-5p activity and result in de-differentiation of the one or more cells. Certain aspects of the invention provide methods and compounds that may be used to enhance activity of miRNA-873-5p and/or miRNA-518d-5p in a cell, which decreases GNMT enzyme activity in the cell. Molecules and compounds that enhance activity of miRNA-873-5p and/or an miRNA-518d-5p are referred to herein as microRNA-enhancer compounds. A microRNA-enhancer compound increases the ability of its target miRNA to act on the miRNA's target mRNA, thus it may increase transcription of protein from the target mRNA. As used herein the term "target miRNA" means the miRNA whose activity is to be increased by the miRNA-enhancer compound. In certain aspects of the invention the target microRNA is miRNA-873-5p. In some embodiments, methods of the invention include contacting a cell with an miRNA-enhancer compound in an amount that is effective to decrease GNMT enzyme activity in the cell. In some embodiments, methods of the invention include contacting a cell, tissue, or organ with an miRNA-enhancer compound in an amount that is effective to increase DNA hypermethylation in the cell, tissue, organ. In certain aspects of the invention a contacted or treated cell is a cultured cell, an in vitro cell, an in vivo cell, or an ex vivo cell.

Cells, Subjects, and Controls

Methods of the invention may be used in conjunction with cells, tissues, organs and/or subjects. In some aspects of the invention a subject is a human or vertebrate mammal including but not limited to a dog, cat, horse, cow, goat, mouse, rat, and primate, e.g., monkey. Thus, the invention can be used to treat diseases or conditions in human and non-human subjects. In some aspects of the invention a subject may be a farm animal, a zoo animal, a domesticated animal or non-domesticated animal and methods of the invention can be used in veterinary prevention and treatment regimens. In some embodiments of the invention, the subject is a human and methods of the invention can be used in human prevention and treatment regimens.

Non-limiting examples of subjects to which the present invention can be applied are subjects who are diagnosed with, suspected of having, or at risk of having, a liver disease or condition. Methods of the invention may be applied to a subject who, at the time of treatment, has been diagnosed as having a liver disease or condition, or a subject who is considered to be at risk for having or developing a liver disease or condition. In some aspects of the invention a liver disease or condition is an acute liver disease or condition, and in certain aspects of the invention a liver disease or condition is a chronic liver disease or condition.

A cell to which methods of the invention may be applied include cells that are in vitro, in vivo, ex vivo cells. Cells may be in a subject, in culture, and/or in suspension, or in any other suitable state of condition. A cell to which a method of the invention may be applied can be a liver cell or other type of vertebrate cell, included human and non-human mammalian cells. In certain aspects of the invention, a cell to which methods of the invention may be applied is a healthy, normal cell that is not a liver cancer cell. In certain embodiments of the invention a cell to which methods of the invention may be applied is one or more of a liver cancer cell, a metastatic cancer cell, a precancerous liver cell, a cirrhotic liver cell, a post-cancer liver cell, a fibrotic liver cell, a hepatocyte, an inflammatory liver cancer cell, and a chemoresistant liver cell. In certain embodiments of the invention a cell that is contacted with a microRNA-modulator is a liver cancer cell, a metastatic cancer cell, a precancerous liver cell, a cirrhotic liver cell, a post-cancer liver cell, a fibrotic liver cell, a hepatocyte, an inflammatory liver cancer cell, and a chemoresistant liver cell. In certain aspects of the invention, a control cell is a normal cell, but it will be understood that a cell having a disease or condition (for example but not limited to a liver disease or condition) may also serve as a control cell in particular circumstances for example to compare results in a treated cell having a disease or condition versus an untreated cell having the disease or condition, etc.

A level of GNMT, miRNA-873-5p, and/or miRNA-518d-5p activity can be determined and compared to control level of GNMT, miRNA-873-5p, and/or miRNA-518d-5p activity, respectively, according to methods of the invention. A control may be a predetermined value, which can take a variety of forms. It can be a single cut-off value, such as a median or mean. It can be established based upon comparative groups, such as in groups having normal levels of GNMT, miRNA-873-5p, and/or miRNA-518d-5p activity and groups having reduced levels of GNMT, miRNA-873-5p, and/or miRNA-518d-5p activity. Another example of comparative groups may be groups having one or more symptoms of or a diagnosis of a liver disease or condition and groups without having one or more symptoms of or a diagnosis of the liver disease or condition. Typically, a control may be based on apparently healthy normal individuals in an appropriate age bracket or apparently healthy cells. It will be understood that controls according to the invention may be, in addition to predetermined values, samples of materials tested in parallel with the experimental materials. Examples include samples from control populations or control samples generated through manufacture to be tested in parallel with the experimental samples.

In some aspects of the invention, values of one or more of GNMT, miRNA-873-5p, and miRNA-518d-5p activity determined for a subject may serve as control values for later determinations of GNMT, miRNA-873-5p, and miRNA-518d-5p activity, respectively, in that same subject, thus permitting assessment of changes from a "baseline" GNMT, miRNA-873-5p, and miRNA-518d-5p activity in a subject. Thus, an initial GNMT, miRNA-873-5p, and miRNA-518d-5p activity level may be present and/or determined in a subject, cell, or tissue and methods and compounds of the invention may be used to decrease the level of miRNA-873-5p, and miRNA-518d-5p activity and increase the level of GNMT activity in the subject, with the initial level serving as a control level for that subject. Using methods and microRNA-inhibitor compounds of the invention, a level of miRNA-873-5p and/or miRNA-518d-5p activity in a cell and/or subject may be decreased by at least 0.5%, 1%, 5%, 10%, 20%, 30%, 40%, 50%, 60%, 70%, 80%, 90% or more compared to the initial level as a treatment for a liver disease or condition in the cell and/or subject, respectively, or compared to a non-contacted control level in a cell and/or subject, respectively. Using methods and microRNA-inhibitor compounds of the invention, a level of GNMT activity in a cell and/or subject may be increased by at least 1%, 5%, 10%, 20%, 30%, 40%, 50%, 60%, 70%, 80%, 90%, 100%, 125%, 150%, 250%, 500%, 1000%, 5000%, or more compared to the initial level as a treatment for a liver disease or condition in the cell and/or subject, respectively, or compared to a non-contacted control level in a cell and/or subject, respectively.

Using methods and microRNA-enhancer compounds of the invention, a level of miRNA-873-5p and/or miRNA-518d-5p activity in a cell and/or subject may be increased by at least 0.5%, 1%, 5%, 10%, 20%, 30%, 40%, 50%, 60%, 70%, 80%, 90%, 100%, 125%, 150%, 250%, 500%, 1000%, 5000%, or more after contact with the microRNA-enhancer compound as compared to the initial level in the cell prior to such contact or as compared to a non-contacted control cell level. Using methods and microRNA-enhancer compounds of the invention, a level of GNMT activity in a cell and/or subject may be decreased by at least 0.5%, 1%, 5%, 10%, 20%, 30%, 40%, 50%, 60%, 70%, 80%, 90% or more compared to the initial level in the cell prior to such contact or as compared to a non-contacted control cell level.

Treatment

Liver diseases and conditions are examples of diseases and conditions that may be treated using methods of the invention to inhibit miRNA-873-5p and/or miRNA-518d-5p activity and/or to increase GNMT. Liver diseases and conditions that may be treated with microRNA-inhibitors in methods of the invention, include, but are not limited to: a liver cancer, a metastatic cancer in the liver, a precancerous liver condition, hepatocellular carcinoma, cirrhosis, a post-cancer liver condition, non-alcoholic fatty liver disease (NAFLD), fatty liver, liver inflammation, liver fibrosis, non-alcoholic steatohepatitis (NASH), cryptogenic cirrhosis, hepatocelullar carcinoma, decompensated liver, steatohepatitis, and chemoresistance. In some embodiments, methods of the invention may be used to reduce chemoresistance and to reduce tumor growth and recurrence in a subject. Administration of a microRNA-inhibitor compound can be useful to reduce chemoresistance in a subject being treated for cancer, and can increase the likelihood of successful cancer therapy with a more positive therapeutic outcome for the subject, than would be present in the absence of the treatment method of the invention. Thus, administration of a microRNA-inhibitor of the invention may reduce chemoresistance in a subject who is being treated with a chemotherapeutic agent or will be treated with a chemotherapeutic agent.

In certain aspects of the invention, a subject may be administered a microRNA-inhibitor compound at a time that is one or more of before or after diagnosis of a liver disease or condition. In some aspects of the invention, a subject is at risk of having or developing a liver disease or condition. A subject at risk of developing a liver disease or condition is one who has an increased probability of developing the liver disease or condition, compared to a control risk of developing the liver disease or condition. In some embodiments of the invention, a level of risk may be statistically significant compared to a control level of risk. A subject at risk may include, for instance, a subject who is, will be, a subject who has a preexisting disease and/or a genetic abnormality that makes the subject more susceptible to a liver disease or condition than a control subject without the preexisting disease or genetic abnormality; a subject having a family and/or personal medical history of a liver disease or condition; and a subject who has previously been treated for the liver disease or condition. It will be understood that a preexisting disease and/or a genetic abnormality that makes the subject more susceptible to a liver disease or condition, may be a disease or genetic abnormality that when present has been previously identified as having a correlative relation to a higher likelihood of developing a liver disease or condition.

As used herein, the terms "treat", "treated", or "treating" when used with respect to a liver disease or condition may refer to a prophylactic treatment that decreases the likelihood of a subject developing the liver disease or condition, and also may refer to a treatment after the subject has developed the liver disease or condition in order to eliminate or reduce the level of the liver disease or condition, prevent the liver disease or condition from becoming more advanced (e.g., more severe), and/or slow the progression of the liver disease or condition in a subject compared to the subject in the absence of the therapy to reduce activity in the subject of one or both of miRNA-873-5p and miRNA-518d-5p and increase the level of GNMT activity in the subject.

Delivering/Administering MicroRNA-Modulator Compounds

MicroRNA-inhibiting compounds of the invention may be administered to a subject in an amount and manner effective to reduce activity of one or both of miRNA-873-5p and miRNA-518d-5p, and/or to increase activity of GNMT enzyme in the subject to treat a liver disease or condition. Methods of the invention, in some embodiments, include administering one or more microRNA-inhibiting compounds to a subject in need of such treatment to reduce a liver disease or condition in the subject. MicroRNA-inhibiting compounds of the invention can be administered to reduce miRNA-873-5p and/or miRNA-518d-5p activity in one more of in vitro, ex vivo, and in vivo cells.

In some embodiments of the invention, activity of one or both of miRNA-873-5p and miRNA-518d-5p may be reduced by genetically introducing a micro-RNA-inhibitor compound into a cell. Targeting agents and methods may be used to aid in delivery of a microRNA-inhibiting compound to a specific cell type, cell subtype, organ, spatial region within a subject, and/or to sub-cellular region within a cell. Art-known methods such as genetic targeting may also be used in embodiments of the invention to control of the amount of a microRNA-modulator compound in a cell and/or subject. Some embodiments of the invention may include a reagent for genetically targeted expression of a microRNA-modulator compound.

A microRNA-modulator compound may be administered in methods of the invention singly or in combination with one or more additional compounds. A microRNA-inhibitor compound administered to a subject or cell to treat a liver disease or condition may act in a synergistic manner with one or more other therapeutic agents or activities and increase the effectiveness of the one or more therapeutic agents or activities and/or to increase the effectiveness of the microRNA-inhibitor compound in treating the liver disease or condition.

Treatment methods of the invention that include administration of a microRNA-inhibitor compound can be used prior to the onset of a liver disease or condition and/or when the liver disease or condition is present, including at an early stage, mid-stage, and late stage of the liver disease or condition and all times before and after any of these stages. Methods of the invention may also be to treat subjects who have previously been treated for a liver disease or condition with one or more other medicaments that were not successful, were minimally successful, and/or are no longer successful at treating the liver disease or condition in the subject.

It will be understood that additional microRNA-inhibitor compounds can be identified and used in treatment methods of the invention. For example, candidate compounds can be can be tested for their ability to decrease activity of one or both of miRNA-873-5p and miRNA-518d-5p, their ability to increase activity of GNMT enzyme and their ability to treat a liver disease or condition using assays and methods presented herein.

Components of MicroRNA-Modulator Compounds

A microRNA-modulator compound useful in methods of the invention may be administered alone or in conjugation with one or more elements such as targeting agents, labeling agents, membrane-crossing delivery agents, sequence tag, etc. in treatment methods of the invention. Thus, in some embodiments of the invention, a microRNA-inhibitor compound consists of a microRNA-inhibitor molecule and in certain embodiments of the invention a microRNA-inhibitor compound comprises a microRNA-inhibitor molecule and one or more additional elements. Similarly, in some embodiments of the invention, a microRNA-enhancer compound consists of a microRNA-enhancer molecule and in certain embodiments of the invention a microRNA-enhancer compound comprises a microRNA-enhancer molecule and one or more additional elements.

Targeting agents useful according to some embodiments of methods of the invention may, include agents that direct a microRNA-modulator compound of the invention to and/or into a cell to be treated such as a liver cell or other type of cell. A targeting compound of choice will depend upon the nature of the liver disease or condition, and on the cell type being targeted. In a non-limiting example, in some embodiments of the invention it may be desirable to target a microRNA-modulator compound to and/or into a liver cell. It will be understood that in some embodiments of methods of the invention, a microRNA-modulator compound includes a microRNA-modulator molecule, without any additional attached elements. For example, in some aspects of the invention a microRNA-modulator may be administered to a cell and/or subject in a "naked" form, meaning no delivery molecules, labels, etc. attached to the microRNA-modulator compound, and in some aspects of the invention a microRNA-modulator may be administered to a cell and/or subject via a transfection means.

In cases where a microRNA-modulator compound is attached to or in a composition with one or more: cell or tissue-carrier agents, targeting agents, labeling agents, delivery agents, etc. a skilled artisan will be aware of and able to select and use suitable agents for use in methods of the invention. In some aspects of the invention, a carrier agent comprises one or more of a nanocarrier, a nanoparticle, a cell-penetrating carrier, a polymer, a dendrimer, a bioconjugate, lipid-based carrier, or other suitable carrier agent. Additional delivery and targeting means and procedures that may be used in aspects of the invention are described in the art. See for example, Torres A. G. 2011, Artif DNA PNA XNA July-December:2(3):71-8, Chen, Z., et al., (2012) Expert Opin Drug Deliv. June; 9(6):649-56, Li, F., & J. Y. Wang (2009) Expert Opin Drug Deliv. May; 6(5):531-41, and Poelstra, K. et al., (2012) J. Control Release July 20; 161(2):188-97, the content of each is incorporated by reference herein in its entirety.

Labeling agents may be used in methods of the invention to determine the location of a microRNA-modulator compound in cells and tissues and also, may be used to assess the cell, tissue, or organ location of treatment compounds that have been administered in methods of the invention. Procedures for attaching and utilizing labeling agents such as enzymatic labels, dyes, radiolabels, etc. are well known in the art.

Effective Amounts

Methods of the invention, in some aspects comprise administering one or more microRNA-inhibitor compounds to a subject in an effective amount for treating a liver disease or condition, or in the case of a microRNA-enhancer compound an effective amount for resulting in de-differentiation of a contacted cell. An "effective amount" used in terms of treating a liver disease or condition, or resulting in cell de-differentiation, is an amount necessary or sufficient to realize a desired biologic effect. For example, an effective amount of a microRNA-inhibitor compound could be that amount necessary to (i) slow or halt progression of the disease or condition; or (ii) reverse, reduce, or eliminate one or more symptoms of the liver disease or condition. In some aspects of the invention, an effective amount is that amount of a microRNA-inhibitor compound that when administered to a subject in need of a treatment of a liver disease or condition, results in a therapeutic response that prevents and/or treats the liver disease or condition. According to some aspects of the invention, an effective amount is that amount of a microRNA-inhibitor compound that when combined or co-administered with another therapeutic treatment for a liver disease or condition, results in a therapeutic response that prevents and/or treats the liver disease or condition. In some embodiments of the invention, a biologic effect of treating a subject with a microRNA-inhibitor compound may be the amelioration and or absolute elimination of symptoms resulting from the liver disease or condition. In some embodiments of the invention, a biologic effect is the complete abrogation of the liver disease or condition, as evidenced for example, by a diagnostic test that indicates the subject is free of the liver disease or condition.

Typically an effective amount of a microRNA-inhibitor compound to decrease activity of miRNA-873-5p or miRNA-518d-5p, and/or to increase activity of GNMT enzyme to a level to treat a liver disease or condition will be determined in clinical trials, establishing an effective dose for a test population versus a control population in a blind study. In some embodiments, an effective amount will be that results in a desired response, e.g., an amount that diminishes a liver disease or condition in cells, tissues, and/or subjects with the liver disease or condition. Thus, an effective amount of a microRNA-inhibitor compound to treat a liver disease or condition that can be treated by reducing activity of miRNA-873-5p or miRNA-518d-5p may be the amount that when administered decreases the amount of miRNA-873-5p or miRNA-518d-5p activity in the subject to an amount that is less than the amount that would be present in the cell, tissue, and/or subject without the administration of the microRNA-inhibitor compound. Similarly, an effective amount of a microRNA-inhibitor compound to treat a liver disease or condition that can be treated by increasing GNMT enzyme activity, may be the amount that when administered increases the amount of GNMT enzyme activity in the subject to an amount that that is more than the amount that would be present in the cell, tissue, and/or subject without the administration of the microRNA-inhibitor compound. In certain aspects of the invention the level of miRNA-873-5p activity, miRNA-518d-5p activity, or GNMT enzyme activity present in a cell, tissue, and/or subject that has not been contacted with or administered a microRNA-inhibitor compound is referred to as a "control" amount. In the case of treating a liver disease or condition the desired response may be reducing or eliminating one or more symptoms of the liver disease or condition in the cell, tissue, and/or subject. The reduction or elimination may be temporary or may be permanent. It will be understood that the status of a liver disease or condition can be monitored using methods of determining miRNA-873-5p activity, miRNA-518d-5p activity, and/or GNMT enzyme activity, symptom evaluation, clinical testing, etc. In some aspects of the invention, a desired response to treatment of the liver disease or condition also can be delaying the onset or even preventing the onset of the liver disease or condition.

An effective amount of a compound that decreases miRNA-873-5p or miRNA-518d-5p activity and/or increases GNMT enzyme activity may also be determined by assessing physiological effects of administration of a microRNA-inhibitor compound on a cell or subject, such as a decrease of a liver disease or condition following administration. Assays and/or symptomatic monitoring of a subject can be used to determine efficacy of a pharmaceutical compound of the invention and to determine the presence or absence of a response to a treatment. An example, though not intended to be limiting, is the use of an art-known test of liver function to determine the status of a liver disease or condition in a subject before and after treatment of the subject with a microRNA-inhibitor compound. It will be understood that the amount of a microRNA-inhibitor compound that is administered to a subject can be modified based, at least in part, on such determinations of disease and/or condition status. The amount of a treatment may be varied for example by increasing or decreasing the amount of a microRNA-inhibitor compound, by changing the composition of the microRNA-inhibitor compound that is administered, by changing the route of administration, by changing the dosage timing and so on. The effective amount of a microRNA-inhibitor compound will vary with the particular condition being treated, the age and physical condition of the subject being treated; the severity of the condition, the duration of the treatment, the nature of the concurrent therapy (if any), the specific route of administration, and additional factors within the knowledge and expertise of the health practitioner. For example, an effective amount may depend upon the desired level of miRNA-873-5p or miRNA-518d-5p activity and/or GNMT enzyme activity that is effective to treat the liver disease or condition. A skilled artisan can empirically determine an effective amount of a particular microRNA-inhibitor for use in methods of the invention without necessitating undue experimentation. Combined with the teachings provided herein, by selecting from among various microRNA-inhibitor compounds and weighing factors such as potency, relative bioavailability, patient body weight, severity of adverse side-effects and preferred mode of administration, an effective prophylactic or therapeutic treatment regimen can be planned that is effective to treat the particular subject.

As used in embodiments of the invention, an effective amount of a microRNA-enhancer compound could be that amount necessary to increase-de-differentiation and/or decrease GNMT enzyme activity of a cell contacted with the microRNA-enhancer compound. In some aspects of the invention, an effective amount is that amount of a microRNA-enhancer compound that when contacted with a cell results in a desired biological effect in the cell.

MicroRNA-Modulating Pharmaceutical Compositions and Dosing

A microRNA-modulator compound that is administered using methods of the invention is also referred to herein as a "pharmaceutical compound". A pharmaceutical compound dosage may be adjusted by an individual health care provider or veterinarian, particularly in the event of any complication. A therapeutically effective amount typically varies from 0.01 mg/kg to about 1000 mg/kg, from about 0.1 mg/kg to about 200 mg/kg, or from about 0.2 mg/kg to about 20 mg/kg, in one or more dose administrations daily, for one or more days. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Methods of the invention may in some embodiments include administering 1, 2, 3, 4, 5, 6, 7, 8, 9, 10, or more doses of a microRNA-inhibitor compound. In some instances, a pharmaceutical compound, (e.g., a microRNA-inhibitor compound, a micro-RNA-enhancer compound, a miRNA-873-5p-inhibitor compound, or a miRNA-518d-5p-inhibitor compound, etc.) can be administered to a subject at least daily, every other day, weekly, every other week, monthly, etc. Doses may be administered once per day or more than once per day, for example, 2, 3, 4, 5, or more times in one 24 hour period.

Methods of the invention, in some aspects, include administration of a pharmaceutical compound alone, in combination with one or more other microRNA-inhibitor compounds, and/or in combination with other drug therapies or treatment activities or regimens that are administered to subjects with a liver disease or condition. Pharmaceutical compounds may be administered in pharmaceutical compositions. Pharmaceutical compositions used in methods of the invention may be sterile and contain an amount of a microRNA-inhibitor compound that will reduce activity of a miRNA-873-5p or a miRNA-518d-5p to a level sufficient to produce the desired response in a unit of weight or volume suitable for administration to a subject. A dose administered to a subject of a pharmaceutical composition that includes a microRNA-inhibitor compound to reduce activity of a miRNA-873-5p or miRNA-518d-5p can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Administration Methods

A variety of administration routes for a microRNA-modulating compound (e.g., a microRNA-inhibitor compound or a microRNA-enhancer compound) are available for use in methods of the invention. The particular delivery mode selected will depend at least in part, upon the particular condition being treated and the dosage required for therapeutic efficacy. Methods of this invention, generally speaking, may be practiced using any mode of administration that is medically acceptable, meaning any mode that produces effective levels of treatment of a liver disease or condition without causing clinically unacceptable adverse effects. In some embodiments of the invention, a microRNA-modulator compound may be administered via an oral, enteral, mucosal, percutaneous, and/or parenteral route. The term "parenteral" includes subcutaneous, intravenous, intramuscular, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial. In some embodiments of the invention, a microRNA-modulator compound may be placed within a slow release matrix and administered by placement of the matrix in the subject. In some aspects of the invention, a microRNA-modulator compound may be delivered to a subject cell using nanoparticles coated with a delivery agent that targets a specific cell or organelle. Various delivery means, methods, agents are known in the art. Non-limiting examples of delivery methods and delivery agents are additionally provided elsewhere herein. In some aspects of the invention, the term "delivering" in reference to a microRNA-modulator may mean administration to a cell or subject of one or more "naked" microRNA-inhibitor compound sequences and in certain aspects of the invention "delivering" means administration to a cell or subject via transfection means. Delivery of a microRNA-modulator compound using a transfection means may include administration of a vector to a cell and/or subject.

In some methods of the invention one or more microRNA-modulator compounds may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. In some embodiments of the invention a microRNA-modulator compound may be formulated with another therapeutic agent for simultaneous administration. According to methods of the invention, a microRNA-modulator compound may be administered in a pharmaceutical composition. In general, a pharmaceutical composition comprises a microRNA-modulator compound and optionally, a pharmaceutically-acceptable carrier. Pharmaceutically-acceptable carriers are well-known to those of ordinary skill in the art. As used herein, a pharmaceutically-acceptable carrier means a non-toxic material that does not interfere with the effectiveness of the biological activity of the active ingredients, e.g., the ability of the microRNA-inhibitor compound, etc. to treat the liver disease or condition. Numerous methods to administer and deliver microRNA-modulator compounds for therapeutic use are known in the art and may be utilized in methods of the invention.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Some embodiments of methods of the invention include administering one or more microRNA-modulating compounds directly to a tissue. In some embodiments, the tissue to which the compound is administered is a tissue in which the liver disease or condition is present or is likely to arise, a non-limiting example of which is the liver. Direct tissue administration may be achieved by direct injection or other means. Many orally delivered compounds naturally travel to and through the liver and some embodiments of treatment methods of the invention include oral administration of one or more microRNA-inhibitor compounds to a subject. MicroRNA-inhibitor compounds, either alone or in conjunction with other therapeutic agents, may be administered once, or alternatively they may be administered in a plurality of administrations. If administered multiple times, the microRNA-inhibitor compounds may be administered via different routes. For example, though not intended to be limiting, a first (or first several) administrations may be made via oral administration and one or more additional administrations may be oral and/or systemic administrations.

For embodiments of the invention in which it is desirable to administer a microRNA-inhibitor compound systemically, the microRNA-inhibitor compound may be formulated for parenteral administration by injection, e.g., by bolus injection or continuous infusion. Formulations for injection may be presented in unit dosage form, e.g., in ampoules or in multi-dose containers, with or without an added preservative. MicroRNA-modulator compound formulations (also referred to as pharmaceutical compositions) may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of one or more microRNA-inhibitor compounds and to achieve appropriate reduction in activity of miRNA-873-5p or miRNA-518d-5p.

In yet other embodiments, methods of the invention include use of a delivery vehicle such as biocompatible microparticle, nanoparticle, or implant suitable for implantation into a recipient, e.g., a subject. Exemplary bioerodible implants that may be useful in accordance with this method are described in PCT Publication No. WO 95/24929 (incorporated by reference herein), which describes a biocompatible, biodegradable polymeric matrix for containing a biological macromolecule. Such delivery means are well known in the art and can be used to achieve sustained release of a microRNA-modulator compound in a subject, and may be selected not to degrade, but rather, to release by diffusion over an extended period of time.

Both non-biodegradable and biodegradable polymeric matrices can be used in methods of the invention to deliver one or more microRNA-modulating compounds to a subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In general, microRNA-modulating compounds may be delivered in some embodiments of the invention using the bioerodible implant by way of diffusion, or by degradation of the polymeric matrix. Exemplary synthetic polymers for such use are well known in the art. Biodegradable polymers and non-biodegradable polymers can be used for delivery of microRNA-modulator compounds using art-known methods. Bioadhesive polymers such as bioerodible hydrogels (see H. S. Sawhney, C. P. Pathak and J. A. Hubell in Macromolecules, 1993, 26, 581-587, the teachings of which are incorporated by reference herein) may also be used to deliver microRNA-inhibitor compounds for treatment of a liver disease or condition. Additional suitable delivery systems can include time-release, delayed release or sustained release delivery systems. Such systems can avoid repeated administrations of a microRNA-modulator compound, increasing convenience to the subject and the medical care professional. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be suitable for prophylactic treatment of subjects and for subjects at risk of developing a recurrent liver disease or condition. Long-term release, as used herein, means that the implant is constructed and arranged to deliver a therapeutic level of a microRNA-inhibitor compound for at least up to 10 days, 20 days, 30 days, 60 days, 90 days or longer. Long-term sustained release implants are well-known to those of ordinary skill in the art and include some of the release systems described above.

Therapeutic formulations of microRNA-modulator compounds may be prepared for storage by mixing the molecule or compound having the desired degree of purity with optional pharmaceutically acceptable carriers, excipients or stabilizers [Remington's Pharmaceutical Sciences 21$^{st}$ edition, (2006)], in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Assessing Modulator Effects and Treatment Efficacy

Assessment of efficacy of candidate microRNA-modulator compounds to decrease or increase activity of miRNA-873-5p or miRNA-518d-5p in a cell or tissue may also be done using assays of the invention in cells from culture—e.g., as screening assays to assess candidate microRNA-modulating compounds for their ability to increase or decrease miRNA-873-5p or miRNA-518d-5p activity. MicroRNA-inhibitory compounds that reduce miRNA-873-5p or miRNA-518d-5p activity in a cell, tissue, or subject may be used in the treatment of a liver disease or condition and microRNA-enhancer compounds that increase miRNA-873-5p or miRNA-518d-5p activity in a cell or tissue may be used to de-differentiate cells, which may be useful in drug testing, culture, maintenance of cell lines, etc.

Suitable assays may include means to determine microRNA activity, for example activity of miRNA-873-5p or miRNA-518d-5p in cells, tissues, and subjects. Levels of miRNA-873-5p or miRNA-518d-5p activity can be determined in a number of ways when carrying out the various methods of the invention. In some embodiments of the invention, a level of miRNA-873-5p or miRNA-518d-5p activity may be measured in relation to a control level of miRNA-873-5p or miRNA-518d-5p activity, respectively, in a cell, tissue, or subject. One possible measurement of a level of miRNA-873-5p or miRNA-518d-5p activity is a measurement of an absolute level of miRNA-873-5p or miRNA-518d-5p activity. This could be expressed, for example, in a level of miRNA-873-5p or miRNA-518d-5p activity per unit of cells or tissue. Another measurement of a level of miRNA-873-5p or miRNA-518d-5p activity is a measurement of a change in the level and/or activity of miRNA-873-5p or miRNA-518d-5p activity over time and/or a change in the level and/or activity of GNMT enzyme in relevant cells and tissues over time. This may be expressed in an absolute amount or may be expressed in terms of a percentage increase or decrease over time. Activity assays for miRNA-873-5p or miRNA-518d-5p may also be used to assess efficacy of a miRNA-873-5p-inhibitor, miRNA-518d-5p-inhibitor, miRNA-873-5p-enhancer, or miRNA-518d-5p-enhancer compound. In addition, in certain embodiments of the invention, an antibody or antigen-binding fragment thereof that bind polypeptides that are increased or decreased in a manner that correlates with activity of miRNA-873-5p or miRNA-518d-5p may be used to assess activity of miRNA-873-5p or miRNA-518d-5p after contact (e.g., treatment) with a microRNA-modulator compound.

In some embodiments of the invention, a decrease in activity of miRNA-873-5p or miRNA-518d-5p in a cell or tissue, may be a decrease of at least 0.2%, 0.5%, 1.0%, 2.0%, 3.0%, 4.0%, 5.0%, 7.0%, 10%, 15%, 20%, 25%, 30%, 40%, 50%, 60%, 70%, 80%, 90%, or 100% including all values in this range. A decrease in miRNA-873-5p or miRNA-518d-5p activity after contact with a microRNA-inhibitor compound may indicate efficacy of the microRNA-inhibitory compound to treat a liver disease or condition in a subject.

As will be appreciated by those of ordinary skill in the art, the evaluation of a treatment of the invention also may be based upon an evaluation of the symptoms or clinical end-points of a liver disease or condition and such evaluations can be used in conjunction with methods of the invention to assess the status of a liver disease or condition and/or the efficacy of a treatment of a liver disease or condition.

Kits

Also within the scope of the invention are kits that comprise one or more microRNA-modulator compounds such as an miRNA-873-5p-inhibitor compound, an miRNA-518d-5p-inhibitor compound, an miRNA-873-5p-enhancer compound, or an miRNA-518d-5p-enhancer compound and instructions for its use in methods of the invention. Kits of the invention may include one or more of an microRNA-modulator compound that may be used to treat a liver disease or condition, or to contact with one or more cells to result in de-differential on the cell(s). Kits containing microRNA-modulator compounds can be prepared for use in treatment methods of the invention. Components of kits of the invention may be packaged either in aqueous medium or in lyophilized form. A kit of the invention may comprise a carrier being compartmentalized to receive in close confinement therein one or more container means or series of container means such as test tubes, vials, flasks, bottles, syringes, or the like. A first container means or series of container means may contain one or more compounds such as a microRNA-modulator compound. A second container means or series of container means may contain a targeting agent, a labelling agent, a delivery agent, etc. that may be included as a portion of a microRNA-modulator compound to be administered in an embodiment of a treatment method of the invention.

A kit of the invention may also include instructions. Instructions typically will be in written form and will provide guidance for carrying-out a treatment embodied by the kit and for making a determination based upon that treatment.

Methods to Identify Candidate Compounds

Certain aspects of the invention include methods of identifying and/or screening candidate compounds that can be used as microRNA-modulators in methods of the invention to increase or decrease miRNA-873-5p or miRNA-518d-5p activity in cells, tissues, and/or subjects. Methods can include contacting a candidate compound with cells or tissues and/or administering the candidate compound to a subject and determining an amount of miRNA-873-5p or miRNA-518d-5p activity before and after contact of the cells, tissues, and/or subject with the candidate compound. A decrease in the amount of miRNA-873-5p or miRNA-518d-5p activity in comparison to a suitable control is indicative of a compound capable of decreasing the level of miRNA-873-5p or miRNA-518d-5p activity and an increase in the amount of miRNA-873-5p or miRNA-518d-5p activity in comparison to a suitable control is indicative of a compound capable of increasing the level of miRNA-873-5p or miRNA-518d-5p activity.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Material and Methods

Human Samples

Liver DNA and RNA were obtained from HCC patients (described in Table 1) from the BCLC tissue collection (Hospital Clinic, Barcelona, Spain) and 2 healthy livers provided by the Institute of Oncology of Asturias Tumour Bank

TABLE 1

HCC patient information.

| Variable | Cases |
|---|---|
| Total Patients | 35 |
| Male | 25 |
| Female | 10 |
| Age (mean ± sd) | 59.47 ± 12.62 |
| Disease Etiology | |
| HCV | 14 |
| HBV | 10 |
| HCV & HBV | 1 |
| Alcohol Consumption | 4 |
| Alcohol consumption & HBV | 1 |
| Steatohepatitis | 2 |
| Hemochromatosis | 1 |
| Healthy liver | 2 |
| Tumor Size | |
| <5 cm | 25 |
| 5-10 cm | 7 |
| >10 cm | 3 |
| Tumor extension | |
| Single tumor | 32 |
| With satellites or vascular invasion | 12 |
| Multifocal tumor | 3 |

Forty-seven patients with liver cirrhosis and HCC with preserved liver function and corresponded to either BCLC stage A (n=34) and B (n=13) were provided by Dra. Erica Villa (University of Modena and Reggio Emilia, Modena, Italy). Further information is provided in the Villa E., et al, Gut. 2016 May; 65(5):861-9, Epub 2015 Feb. 9. Informed consent was obtained from all the patients included in the study, accordingly with the ethical principles embodied in the Declaration of Helsinki.

Animals

Three-month-old male (C57BL6), GNMT wild type (WT) and Gnmt-knockout (KO) mice were used in the study. Animal procedures were approved following the CIC bioGUNE Animal Facility's guidelines with AAALAC certificate.

Cell Lines

The human hepatoma cell line BCLC3 was previously characterized and provided by Dr. Jordi Bruix and Dra. Loreto Boix (BCLC group Hospital Clinic, Barcelona, Spain). Cells were maintained in DMEM-F12 with 10% FBS.

Isolation and Culture of Primary Hepatocytes

Primary hepatocytes were isolated from male WT Gnmt-KO mice via collagenase perfusion as described in Embade, N. et al., Hepatol, Baltimore, Md. 2012; 55:1237-1248. Adhered cells were maintained in MEM with 10% fetal bovine serum (FBS).

In Vitro Silencing

Primary WT and Gnmt-KO hepatocytes were transfected with miRIDIAN microRNA Hairpin Inhibitor/Mimic hsa-miR-873-5p (Dharmacon, Lafayette, Colo.) using DharmaFECT transfection reagent (Dharmacon) following manufacturers procedure. Controls were transfected with an unrelated siRNA (Sigma-Aldrich, St. Louis, Mo.). Mimic transfection was confirmed by specific miRNA qPCR while inhibitor transfection was confirmed by modulation of its target mRNA GNMT by qPCR and Western blotting.

In Vivo Hsa-miR-873 Inhibition.

Three-month-old male WT mice were injected intravenously in the tail vein with miRIDIAN microRNA Hairpin Inhibitor hsa-miR-873-5p (2.5 µM) or unrelated control siRNA every two days from third day after BDL until seventh day using jetPEI (Polyplus Transfection, Illkirch, France), following manufacturer's instructions. Animals were then sacrificed and livers were removed and snapped frozen in liquid nitrogen or formalin fixed for subsequent analysis.

Immunohistochemistry

Paraffin embedded liver samples were sectioned, dewaxed and hydrated. Immunohistochemistry was performed as described in Barbier-Torres, L., et al., Oncotarget 2015; 6:2509-2523.

Drug Treatments

Primary hepatocytes cultured overnight in MEM (0% FBS) were treated with deoxycholic acid (DCA) 100 µM for indicated times.

microRNA Quantitative Real-Time PCR

Specific RT-PCR was performed for each of the miRNAs analyzed following TaqMan® MicroRNA Reverse Transcription Kit procedure. 10-50 ng of RNA were used for the reaction. Quantitative PCR was performed with TaqMan Universal PCR Master Mix No AmpErase UNG kit (Life Technologies, Carlsbad, Calif.) and specific primers for each miRNA following manufacturers procedure. In every case, each miRNA analyzed was normalized with the U6 snRNA miRNA.

Apoptosis Measurement

Caspase 3 activity assay was performed as described in Embade N., et al., Hepatol. Baltim. Md. (2012); 55:1237-1248.

Luciferase Reporter Assay

Murine and human GNMT cDNA sequences were purchased from Source biosciences (cDNA clone MGC: 13738 IMAGE: 4210236 and cDNA clone MGC:45044 IMAGE: 5229272 respectively). Their 3'UTR sequences were subcloned into the pmirGLO vector (Promega, Sunnyvale, Calif.) obtaining the pmirGLO-GNMT-3'UTR. Hepatocytes and BCLC3 cells were transfected with the pmirGLO or pmirGLO-GNMT-3'UTRvector together with miRIDIAN microRNA Hairpin Inhibitor/Mimic hsa-miR-873-5p or non-related siRNA using DharmaFECT Duo Transfection Reagent (Dharmacon) in MEM or DMEM-F12, respectively. The activities of firefly and *Renilla luciferases* in cell lysates were determined with a dual-luciferase assay system (Promega). Normalized data were calculated as the ratio of firefly luciferase/*Renilla* activities.

SAMe Measurement

Hepatic S-adenosylmethionine (SAMe) and S-adenosylhomocysteine (SAH) were determined by LC/MS using a Waters ACQUITY-UPLC system coupled to a Waters Micromass LCT Premier Mass Spectrometer equipped with a Lockspray ionization source as described in Martinez-Lopez N., et al., Gastroenterology (2012); 143:787-798e13. Global DNA Methylation Measurement. Quantification of 5mC by Mass Spectrometry Global DNA methylation (5mC) and hydroxymethylation (5hmC) analyzes were performed following the method described in Le, T. et al., Anal. Biochem. (2011); 412:203-209.

Statistical Analysis

Data are expressed as mean±SEM. Statistical significance was determined by Student's t test or Welch's test whenever unequal variances were found, where indicated. A p value<0.05 was considered as significant.

Results

Identification of the miRNAs Targeting GNMT Expression.

Figure 6B:
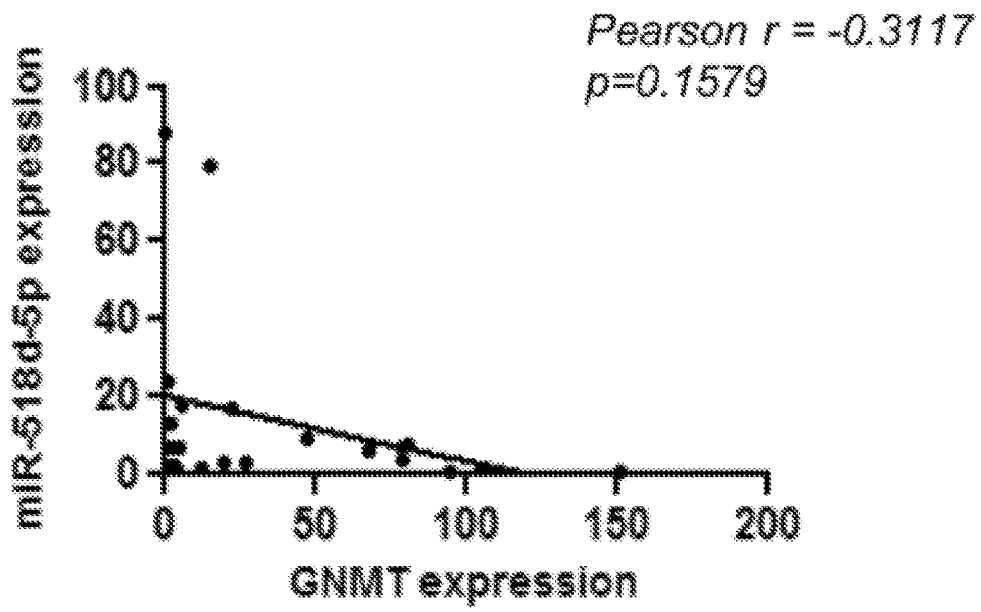

To identify miRNAs that could control GNMT expression three independent, unbiased approaches were utilized: TargetScanHuman, MicroCosm, and microRNA. From the broad spectrum of all database-coincident miRNAs retrieved from the analysis, those with higher scores that appear induced in the miRNA panel in the human hepatoma BCLC cells were selected (FIG. 6A). Both miRNA-873-5p and miRNA-518d-5p were found to be induced in most of those hepatoma cells versus healthy normal liver (FIG. 6A). In addition, the expression of these miRNAs and GNMT levels were evaluated in a selected cohort of HCC patient tumor samples (characteristics of the patients are described in Table 1). A significant statistical correlation was found between liver tumors with low GNMT expression and high miR-873-5p (FIG. 1A left panel), while in the case of miRNA-518d-5p no association was identified (FIG. 6B). Furthermore, comparing paired cirrhotic tissue to their non-cirrhotic tissue identified an important difference in miR-873-5p expression levels and a significant negative correlation between miR-873-5p and GNMT expression levels (FIG. 1A right panel).

Figure 1B:
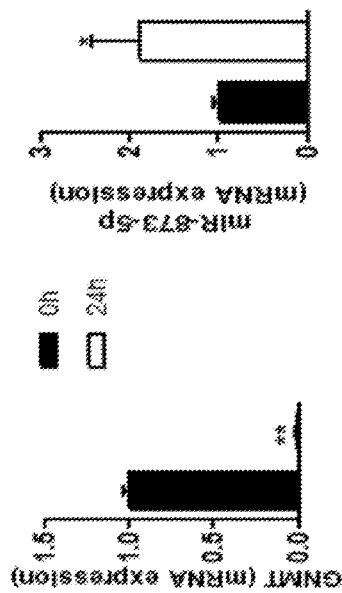
Figure 1C:
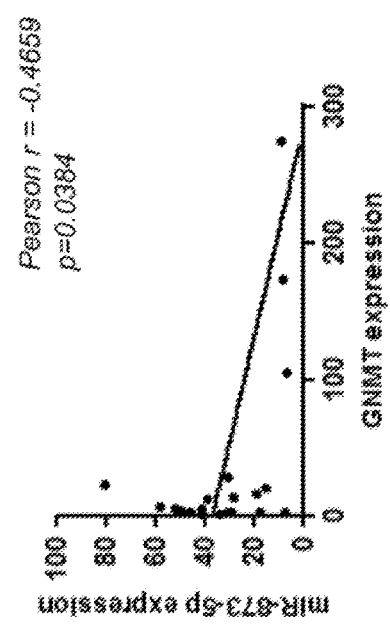
Figure 1C:
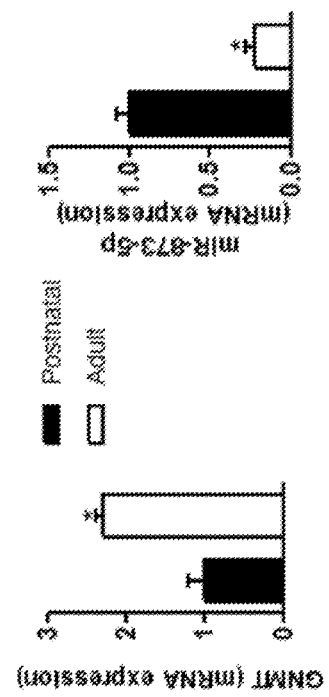

Although GNMT is mainly expressed in adult liver, in the postnatal organ the expression is minimal Experimental results indicated that the increase of GNMT levels in well-differentiated hepatocytes was accompanied with a reduction of miR-873-5p levels (FIG. 1B). On the contrary, during the de-differentiation of primary hepatocytes in culture, a decrease in GNMT expression was observed that notably correlated with an increase of miR-873-5p levels (FIG. 1C).

The association between miR-873-5p and GNMT levels was further investigated in liver injury mouse models, such as bile duct ligation (BDL)-induced liver fibrosis. Under these circumstances, GNMT mRNA expression was reduced after 1, 3 and 7 days of BDL association with a marked increase of miR-873-5p expression (FIG. 1D). BDL-induced liver fibrosis is a direct consequence of accumulation of bile acids in the liver and treatment of primary hepatocytes with the bile acid, deoxycholic acid (DCA), resulted in the observation of a down regulation of GNMT expression accompanied with an elevation of the miR-873-5p levels (FIG. 1E). Taken together, these findings suggest that an alteration in the expression of the miR-873-5p is closely associated with changes of hepatic GNMT levels both in liver differentiation and liver injury, supporting its role in the regulation of GNMT expression GNMT 3 VTR Contains a Binding Site for the miR-873-5p.

Figure 6C:
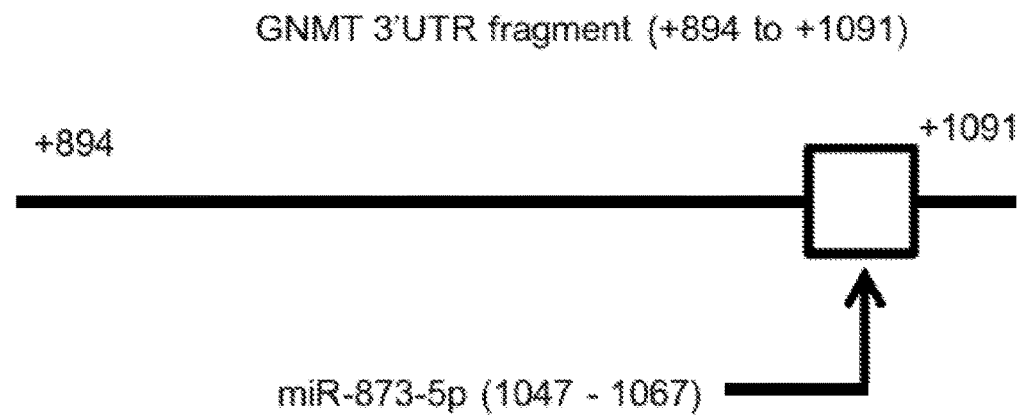
Figure 8:
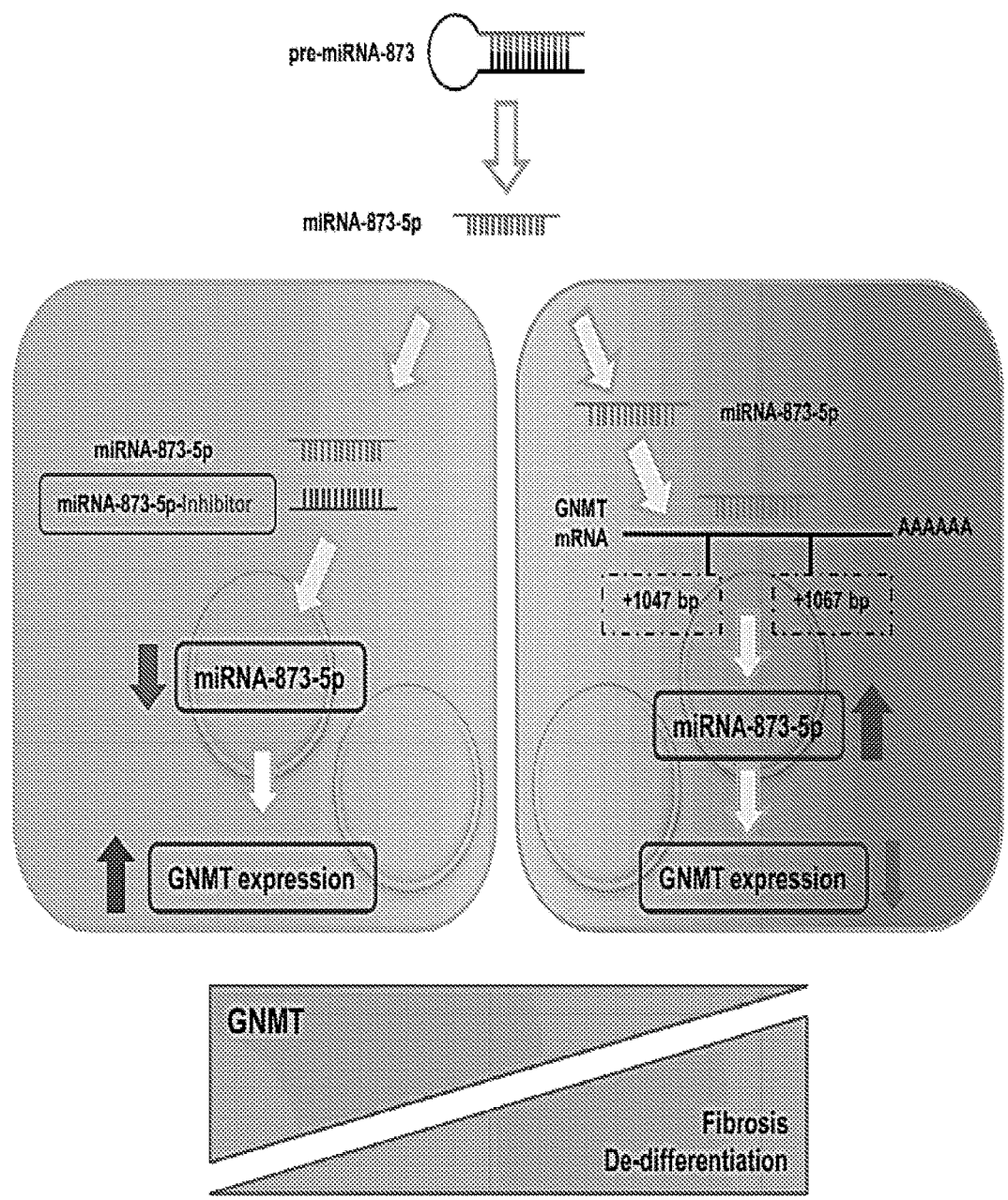
FIG. 8 is a schematic diagram illustrating miR-873-5p inhibition blocking liver de-differentiation and fibrosis targeting GNMT expression. The schematic represents the effect of miRNA-873-5p in the liver on the regulation of GNMT expression, affecting liver de-differentiation and fibrotic phenotype. On the left, the effect of inhibiting miR-873-5p recovering GNMT expression is shown.

To investigate how miR-873-5p regulated GNMT expression, the 3'UTR of GNMT was fused to a luciferase reporter gene and cloned into the pmirGLO vector (pmirGLO-GNMT-3'UTR). FIG. 6C shows the putative binding site for the miR-873-5p in the 3'UTR of GNMT. Luciferase activity revealed that in primary wild type mouse hepatocytes, the transfection with the mimic miR-873-5p rendered approximately a 50% decrease of the reporter activity of the 3'UTR GNMT in comparison to those transfected with control miRNA (FIG. 1F, left panel). On the other hand, the response of luciferase activity driven by pmirGLO-GNMT-3'UTR in BCLC3 cells (characterized by high levels of hsa-miR-873-5p) revealed a reduction of this reporter activity even at basal levels that was neutralized after silencing miR-873-5p by a specific inhibitor (FIG. 1F, right panel). Overall, these results supported a role for miR-873-5p as a key player in the regulation of GNMT expression.

miR-873-5p Inhibition Keeps Primary Hepatocytes Differentiated.

GNMT is a marker of liver differentiation (see Aliva, M. A., et al., J. Hepatol. 2000; 33:907-914). To evaluate whether changes in the expression of miR-873-5p counteracted the de-differentiation that primary hepatocytes undergo in culture, miR-873-5p was inhibited with its specific inhibitor. The results indicated that GNMT levels were gradually reduced with increased time in culture. In addition, the ablation of miR-873-5p increased GNMT expression both at mRNA and protein level during the de-differentiation process (FIG. 2A-D). Significantly, pivotal differentiation markers like the hepatocyte nuclear factor 4a (HNF4a) and those genes related with normal differentiated liver such as albumin, and hexokinase 4 (HK4) were partially re-stabilized after blocking the miR-873-5p (FIG. 2B). Likewise, the expression of genes and proteins related with a de-differentiated phenotype like pyruvate kinase M2 isoform (PKM2), alfa-fetoprotein (AFP) (FIG. 2C) and glutaminase 1 (GLS1) (data not shown) were reduced. A well-preserve Cytochrome P450 genes (CYPs) detoxification system in primary hepatocytes was found after miR-873-5p inhibition (FIG. 2D). The results supported a finding that maintaining the levels of miR-873-5p under a controlled down-regulation had a significant impact on the hepatic phenotype. Notably, it was also identified that the increase in GNMT expression upon hsa-miR-873-5p knockdown in primary hepatocytes in culture elevated the levels of the mitogenic factor hepatocyte growth factor (HGF) that induced the activation of S6K, the phosphorylation of S6 (Thr389) and the elevation of 4EBP1 (Th37/46) as described previously. (See Yen, C.-H., et al., Mol. Med. 2011:18; 286-296).

Remarkably, inhibition of miR-873-5p in primary hepatocytes derived from the Gnmt-KO mice failed to counteract the loss of the hepatic phenotype, further highlighting the specificity of miR-873-5p in GNMT expression during liver de-differentiation (FIG. 7A). However, it is important to note that miR-873-5p is not regulated in de-differentiation in Gnmt-KO hepatocytes.

Inhibition of miR-873-5p Attenuates Liver Damage after Bile Duct Ligation.

Figure 3D:
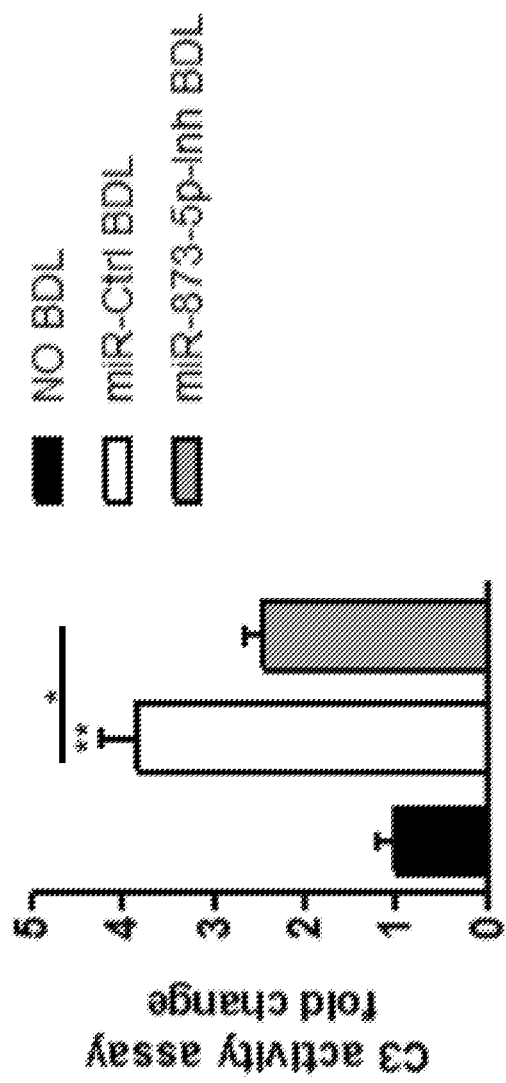
Figure 3E:
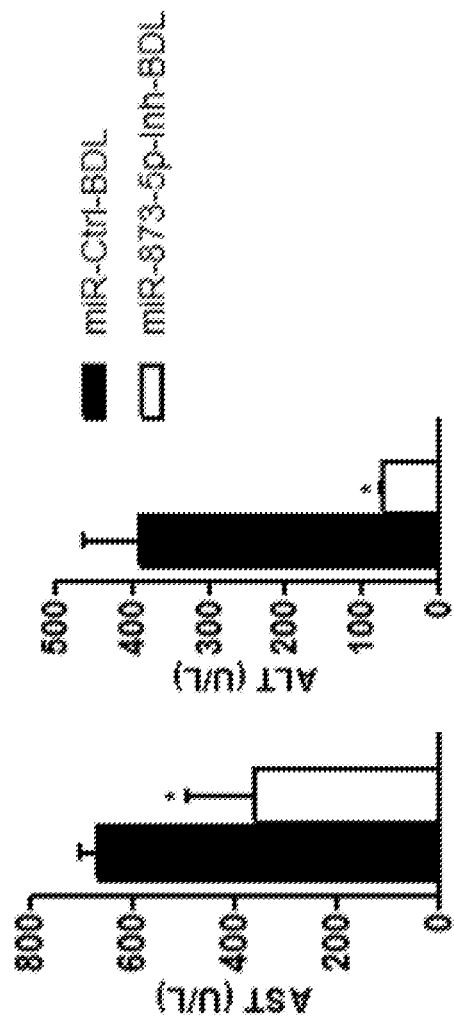
Figure 3F:
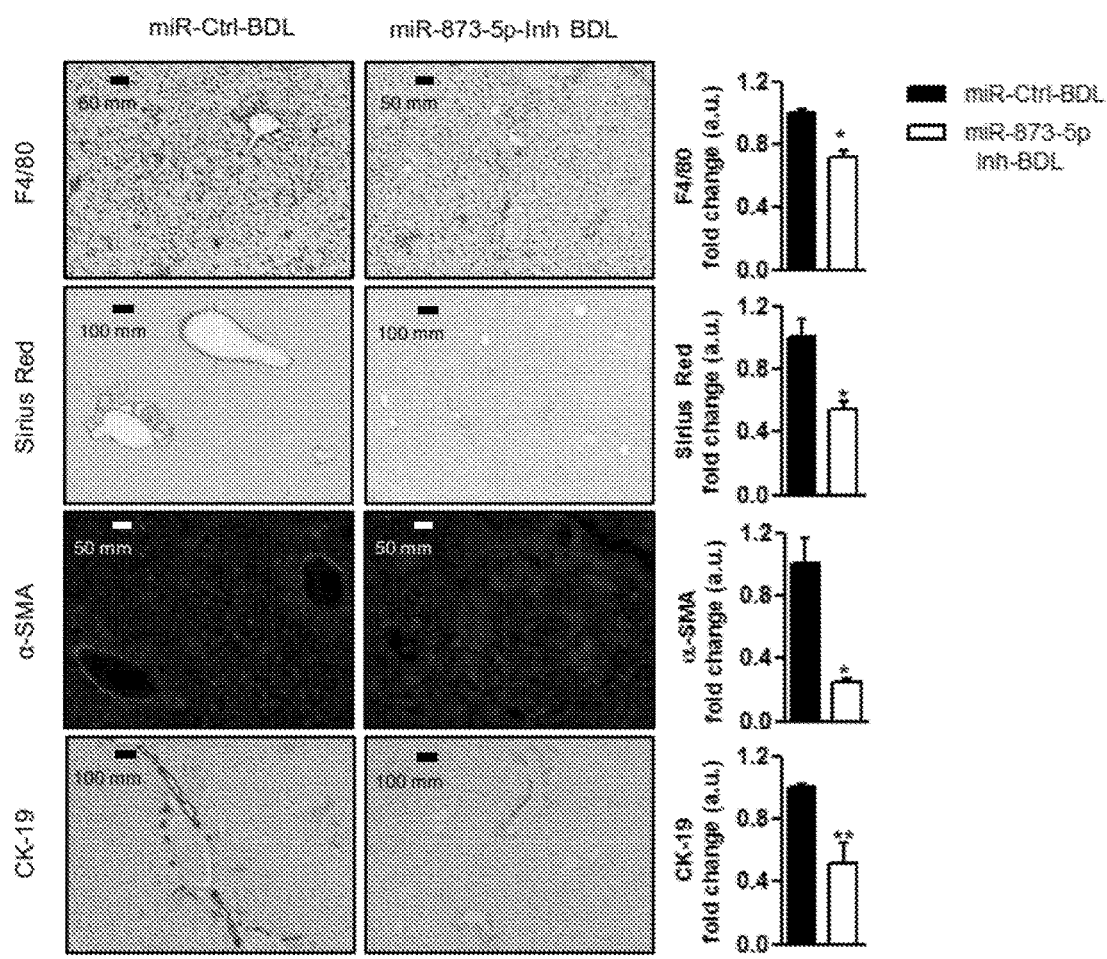

To evaluate if changes in miR-873-5p and GNMT play an important role in liver injury, the levels of the miR-873-5p were modulated by i.v. injection with the specific inhibitor of this miRNA in the BDL-induced fibrosis mouse model starting three days post-surgery, when an inflammatory response and alteration in the bile acid homeostasis are taking place in the liver. It was found that miR-873-5p inhibition in BDL rodents restored GNMT mRNA and protein expression to normal values (FIG. 3A upper and lower panel). The specific inhibition of miR-873-5p dramatically increased the survival percentage of the mice after BDL—up to 100%, as compared to less than 40% survival percentage in the miR-control treated mice (FIG. 3C). This effect was accompanied with a significant reduction in caspase 3 activity, in the cleavage of PARP as a readout of apoptotic activity and finally in the levels of ALT and AST (FIG. 3A-E). In addition, staining for inflammatory markers like F4/80, and the evidences for fibrogenic indicators as sirius red, alpha smooth actin (α-SMA) and cytokeratin 19 (CK19) were lower in miR-873-5p-inhibited mice as compared to the miR control (FIG. 3F).

Figure 4A:
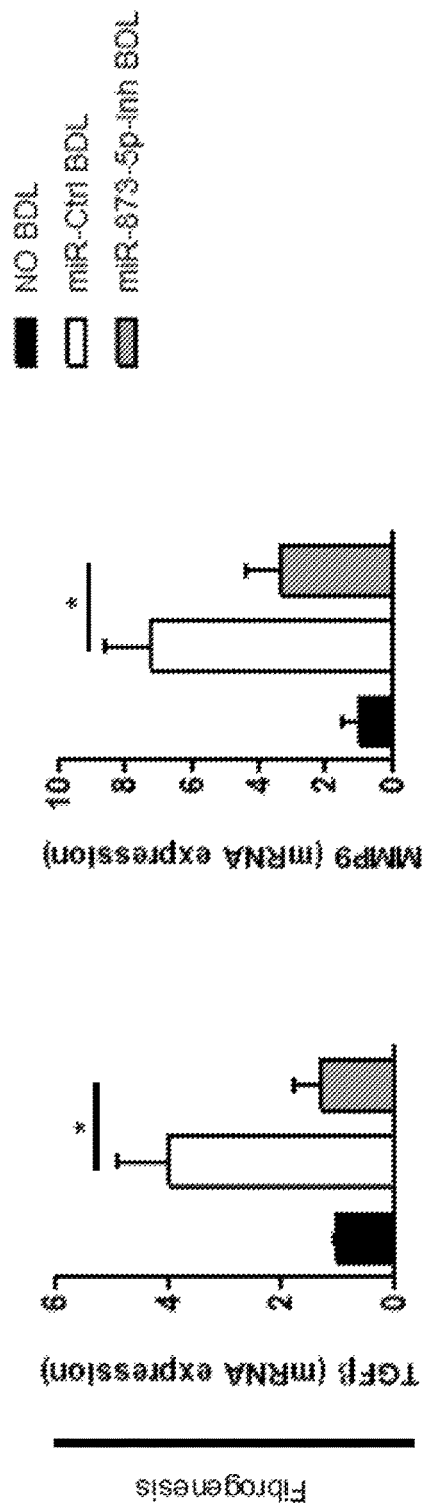
FIG. 4A-C shows graphs of results demonstrating liver damage attenuation in miR-873-5p-inhibited mice after BDL.
Figure 4B:
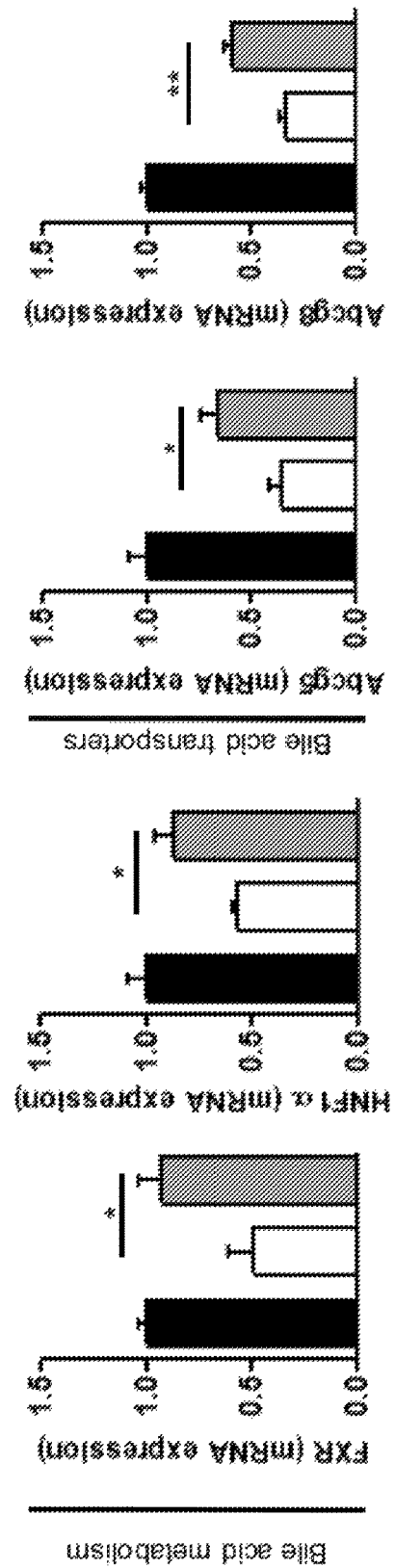

In addition, a reduction in profibrogenic cytokine transforming growth factor beta (TGF-β) expression as well as metalloproteinase 9 (MMP9) expression were detected in the knockdown livers accompanied with a reduction in the activity of JNK and Smad2/3 (FIG. 4A). An intense response was shown in the reprogramming of bile acids metabolism in the miR-873-5p inhibited livers (FIG. 4B), with restored hepatocyte nuclear factor 1 α (HNF1α) and farnesoid X receptor (FXR) expression and induced the active transport of the bile acids through the up regulation of ABCG5 and ABCG8.

Figure 4C:
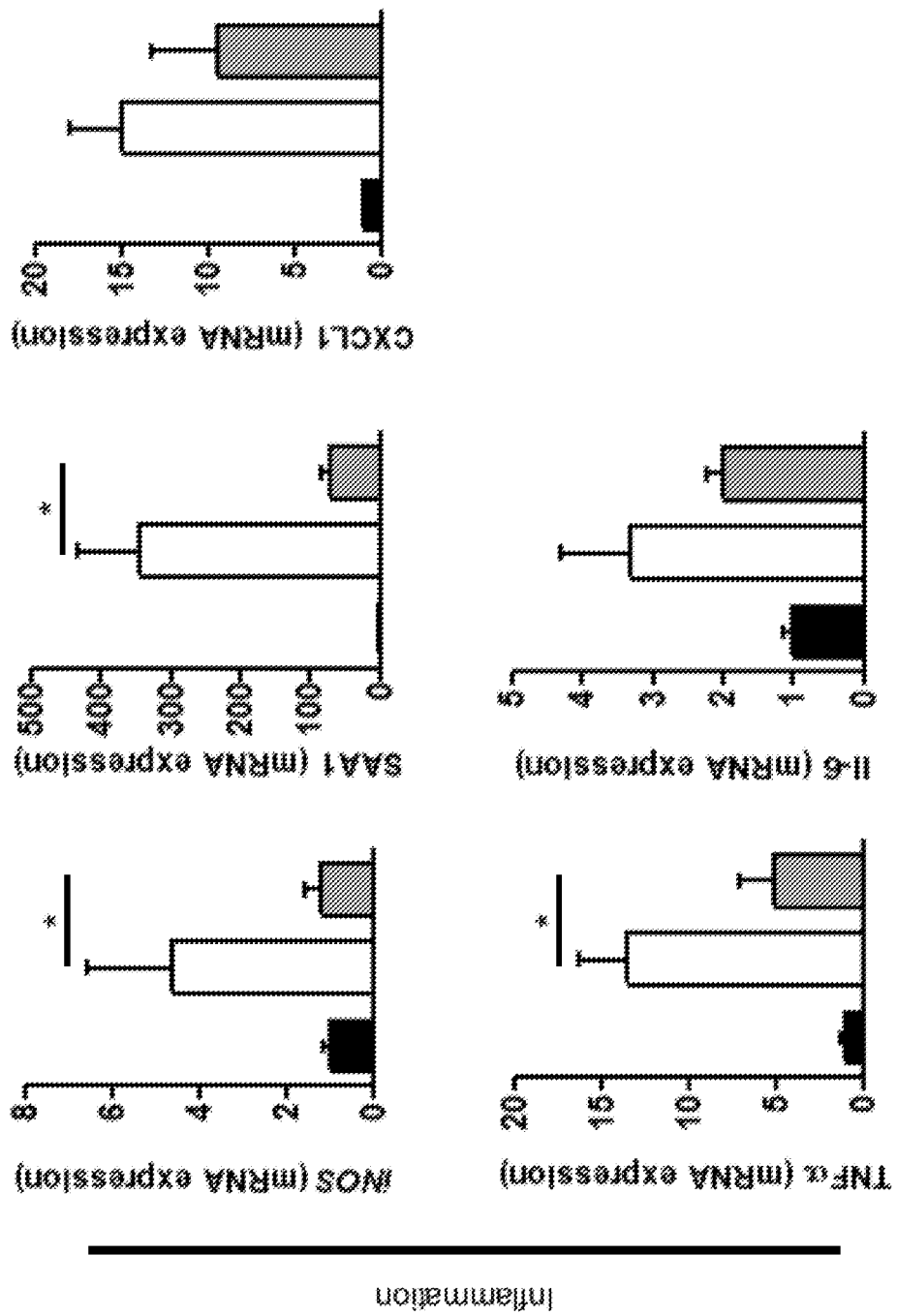

In addition, a reduction in the inflammatory response after BDL was also detected upon miR-873-5p inhibition. This result was demonstrated by a decrease in the inducible nitric oxide synthase (iNOS) expression, in the levels of chemokine receptor directly implicated in immune response, the C-X-C Motif Ligand 1 (CXCL1) and in the acute phase response gene serum amyloid A1 (SAA1) (FIG. 4C). Moreover, a reduction in the proinflammatory signals interleukin-6 (IL-6) and tumor necrosis factor alpha (TNFα) abrogated the response mediated by STAT3 activation after BDL in those livers where GNMT remained up regulated (FIG. 4C).

Overall, the data support a conclusion that miR-873-5p inhibition counteracts the reduction of GNMT during liver damage, blunting the profibrogenic and proinflammatory phenotype associated to the absence of this tumor suppressor gene.

The Absence of miR-873-5p Modulates the Apoptotic Response in Primary Hepatocytes Mediated by Bile Acids.

Figure 5A:
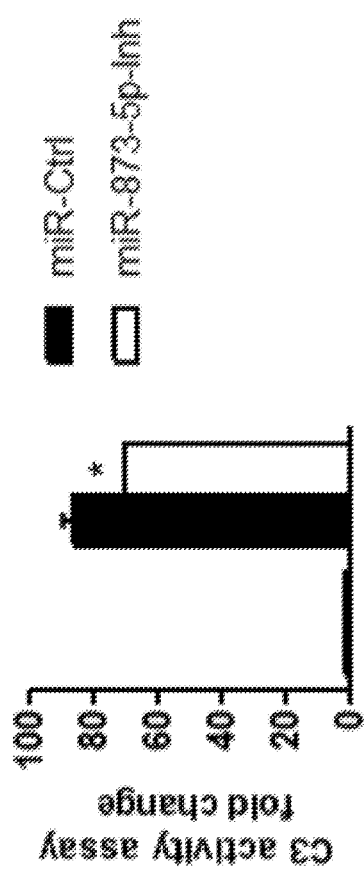
FIG. 5A-D shows graphs of results demonstrating that miR-873-5p inhibition in primary hepatocytes reduces apoptotic response to bile acids.
Figure 5B:
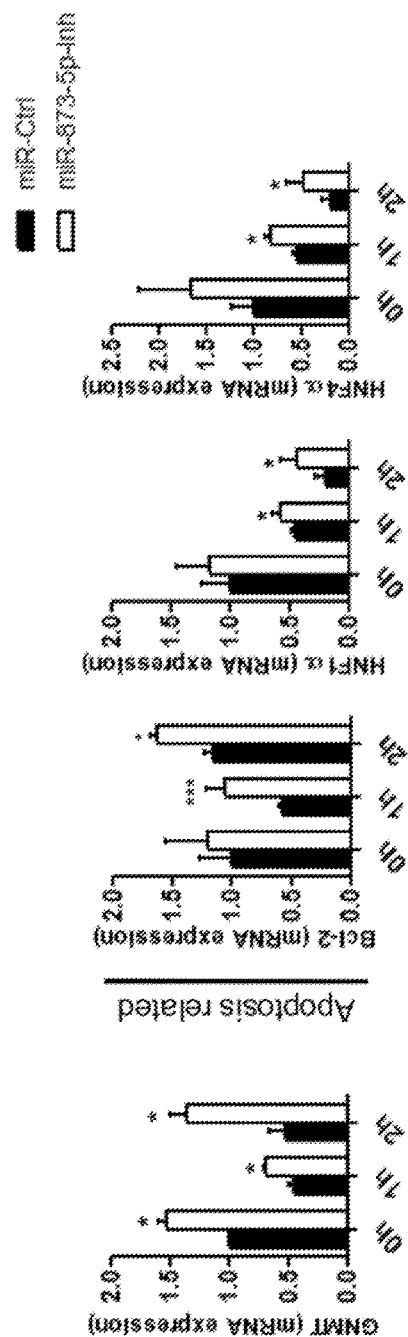
Figure 5C:
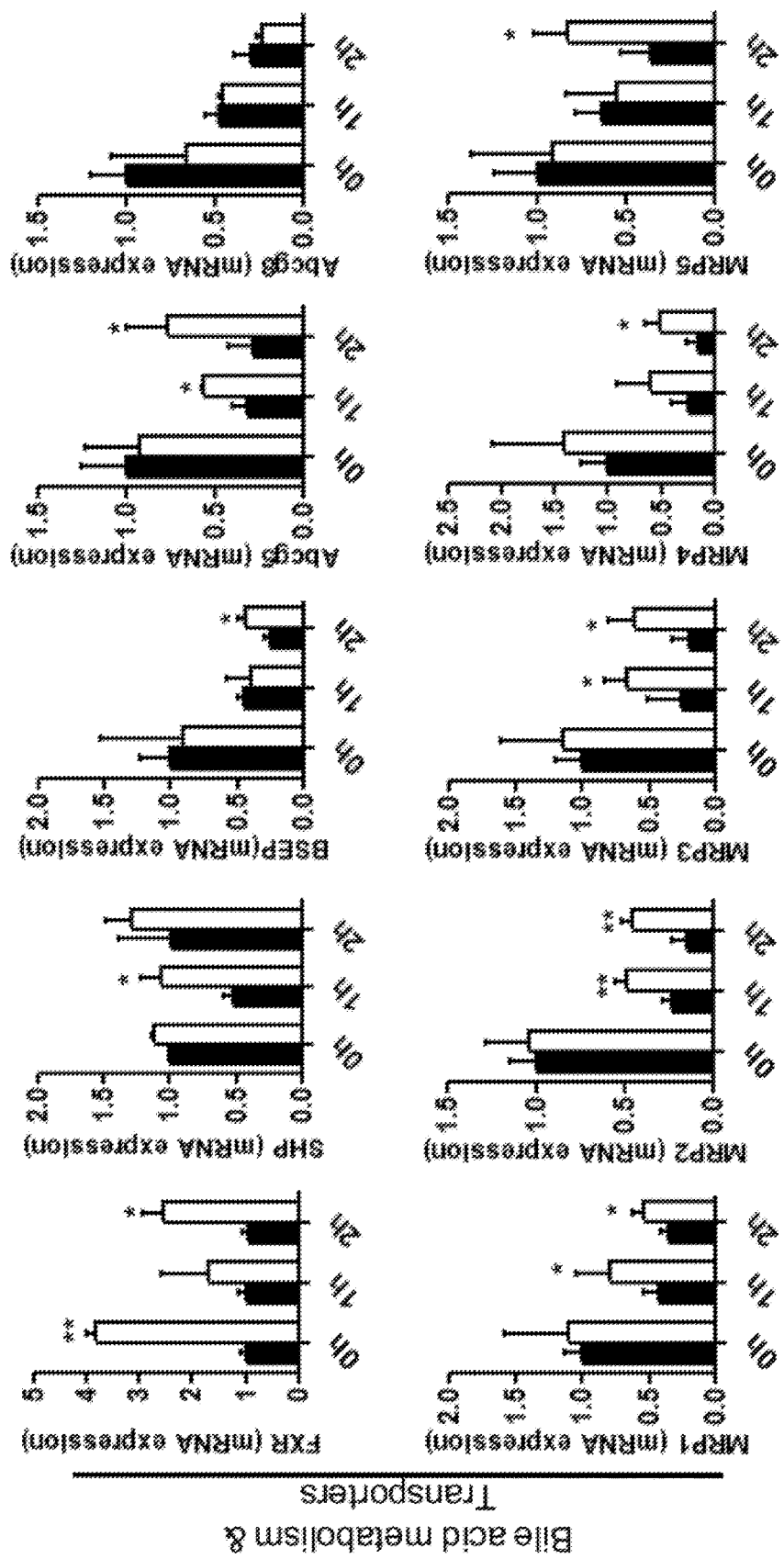
Figure 5D:
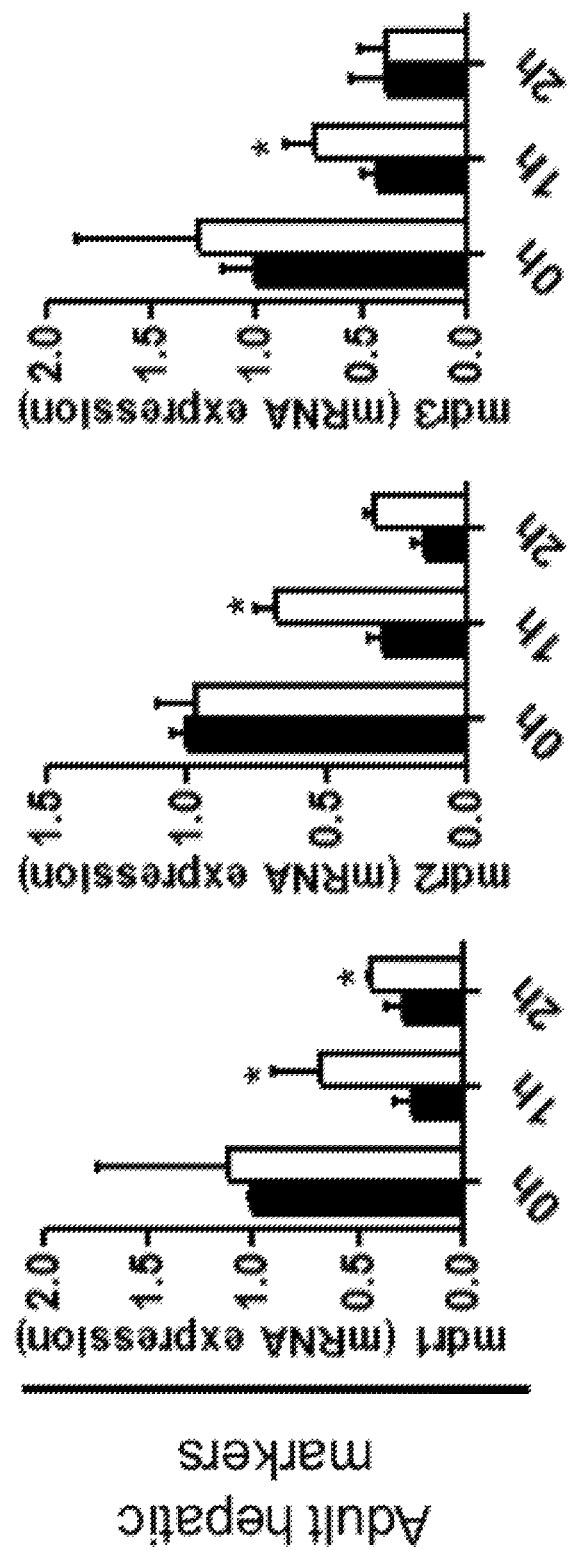

Bile acids are deeply involved in the pathogenesis of BDL-induced injury as well as of clinical fibrosis and cirrhosis. Based on the down regulation of GNMT as a result of elevated miR-873-5p levels after DCA treatment (FIG. 1F), the effect of inhibition of this miRNA was analyzed. Results indicated that blocking miR-873-5p resulted in a reduction of the apoptotic response mediated by caspase 3 activity in primary hepatocytes, in a manner consistent with the corresponding increase in GNMT levels (FIG. 5A). No impact on apoptosis activity was observed after inhibition of miR-873-5p in the Gnmt-KO hepatocytes highlighting the specificity of the effect of miR-873-5p in GNMT expression, and no significant changes on miR-873-5p expression were observed in Gnmt-KO hepatocytes after DCA treatment. The resistance to the apoptotic stimuli mediated by DCA after the ablation of miR-873-5p in wild-type hepatocytes was linked to a significant increase of the apoptotic suppressor Bcl-2 (FIG. 5B). Moreover, a proper regulation of the gene profile associated with bile acid metabolism to preserve liver homeostasis was identified in the absence of miR-873-5p. It has been previously reported that the central mechanism by which bile acids repress the key levels of the transcription factor HNF1α, is through the down regulation of HNF4a (see Jung, D. & Kullak-Ublick G. A., Hepatol. Baltim. Md. 2003; 37:622-631). In addition, ablation of the miR-873-5p 24 hours before kept HNF1α and HNF4a elevated in the presence of DCA (FIG. 5B). The increase of FXR, Bile salt export pump (BSEP) and Small heterodimer partner (SHP) genes and the amount of the ATP Binding Cassette transporters (ABC) MRP1, MRP2, MRP3, MRP4 and MRP5 and ABCG5 associated with stable GNMT levels suggested a less toxic effect of DCA (FIG. 5C). Moreover, the inhibition of miR-873-5p induced the expression of Multi-drug resistance genes (MDRs) MDR1, MDR2 and MDR3 adult hepatic markers (FIG. 5D). Finally, Western blot results indicated that resulting JNK activation decreased notably when the expression of GNMT remained stable and c-jun phosphorylation that appeared to have a protective role in the signaling of DCA increased in the absence of miR-873-5p.

Epigenomic Mechanism Mediated by the Inhibition of Hepatic miR-873-5p-GNMT Dependent.

GNMT is an essential regulator of the total transmethylation flux, implicating this enzyme as an epigenetic controller. Moreover, GNMT was found to be altered in the process of hepatocyte differentiation. As such genes and proteins directly related with SAMe content and methylation reactions (where GNMT plays a fundamental role) like methionine adenosyltransferase (MAT)I/III, the first enzyme responsible of SAMe synthesis, MTA phosphorylase (MTAP), involved in the methionine salvation pathway to regenerative SAMe, and the gene S-adenosylhomocysteine hydrolase (SAHH), that catalyzes the reversible hydrolysis of S-adenosylhomocysteine (AdoHcy) to adenosine (Ado) and L-homocysteine (Hcy) were induced after miR-873-5p inhibition. In addition, the methylenetetrahydrofolate reductase (MTHFR) that catalyzes the conversion of 5,10-methylenetetrahydrofolate to 5-methyltetrahydrofolate, a co-substrate for homocysteine remethylation to methionine was clearly induced after miR-873-5p inhibition. Therefore, inhibition of miR-873-5p maintained the epigenetic status of the differentiated hepatocyte. Indeed knockdown of miR-873-5p significantly blunted the increase in the ratio SAMe/SAH, the index of cellular methylation capacity during hepatocyte de-differentiation (Table 2A).

TABLE 2A

Hepatic SAMe and SAH content in hepatocytes in culture.

| GROUP | SAMe pmol/mg prot Mean ± sd | SAH pmol/mg prot Mean ± sd | SAMe/SAH pmol/mg prot Mean ± sd | T-TEST SAMe/SAH ratio |
|---|---|---|---|---|
| WT | 91.85 ± 0.28 | 28.72 ± 0.81 | 3.20 ± 0.08 | |
| WT 48 h | 67.74 ± 27.29 | 12.86 ± 3.68 | 5.17 ± 0.52 | 0.0002* |
| WT 48 h 873-5p-Inh | 58.48 ± 11.82 | 13.62 ± 1.28 | 4.27 ± 0.38 | 0.0314# |

*p CTRL vs. BDL
p BDL vs. BDL 873-5p-Inh

Likewise, miR-873-5p inhibition in BDL-mouse prevented the increase in SAMe level and SAMe/SAH ratio (Table 2B).

TABLE 2B

Total SAMe and SAH liver content in BDL-mice

| GROUP | SAMe pmol/mg prot Mean ± sd | SAH pmol/mg prot Mean ± sd | SAMe/SAH pmol/mg prot Mean ± sd | T-TEST SAMe/SAH ratio |
|---|---|---|---|---|
| CTRL | 109.06 ± 42.36 | 63.22 ± 12.03 | 1.75 ± 0.72 | |
| BDL | 158.61 ± 34.32 | 41.30 ± 13.93 | 4.00 ± 1.11 | 0.042* |
| BDL 873-5p-Inh | 108.80 ± 38.99 | 58.97 ± 7.57 | 1.86 ± 0.67 | 0.046# |

*p CTRL vs. BDL
p BDL vs. BDL 873-5p-Inh

DNA (CpG) methylation has been described as having a role in global alterations in the epigenome that drives the profibrogenic transformation in the liver (see Mann, D. A., Hepatol. Baltim. Md. 2014; 60:1418-1425). In the experiments described herein, it was found that knocking down miR-873-5p during BDL and increasing GNMT expression prevented the increase in the global DNA (CpG) methylation rate.

The results indicated that the miR-873-5p inhibition post-BDL induced the levels of suppressor of cytokine signaling 3 (SOCS3) and Ras association (RalGDS/AF-6) domain family member (RASSF1A) inhibitors of STAT and RAS pathway in the livers with the corresponding shut down of the STAT3 and c-Raf (Ser259) phosphorylation. These results were in agreement with the repressive effect described previously for SOCS3 and RASSF1A after a chronic silencing of GNMT by hypermethylation of their corresponding promoters (see Martinez-Chantar M. L. et al., Hepatol. Baltim. Md. 2008; 47:1191-1199) and associated with the abnormal grade of proliferation and liver malignant transformation.

Reinforcing this idea, peroxisome proliferator-activated receptor-gamma (PPARγ), a key inhibitor in the myofibroblast transdifferentiation and therefore associated to quiescent hepatic stellate cells phenotype was re-expressed under the inhibition of miR-873-5p post-BDL. The histone lysine methyltransferase, Enhancer of zeste homolog 2 (EZH2), modulates the repression of PPARγ expression (see Mann J. et al., Gastroenterology 2010; 138:704-714, 714.e1-4. It has now been identified that miR-873-5p inhibition through the up regulation of GNMT reduced dramatically the highly representative levels of the profibrogenic hub EZH2 after BDL, both at mRNA and protein levels, thus exerting a pivotal control in the epigenetic network underlying this profibrogenic process, thus supporting a conclusion that the prompt recuperation of hepatic GNMT-miR-873-5p-dependent expression could lead to an epigenetic regulation of specific genes.

Example 2

Material and Methods
Human Samples:
RNA from a cohort of patients with liver cirrhosis was provided by Dr. Javier Crespo (Hospital Universitario Marqués de Valdecilla. Santander) (n=42) and Ramiro Jover (University of Valencia) (n=30). Informed consent was obtained from all the patients included in the study, according to the ethical principles embodied in the Declaration of Helsinki.
Sudan III Methods:
OCT embedded frozen samples were sectioned (8-12 μm thick), cleared with 60% isopropanol, then stained with freshly prepared Sudan III solution (0, 5% in isopropanol Sudan III Panreac Ref: 251731.1606 filtered with a 0.2 mm filter) for one hour and finally cleared again with 60% isopropanol. Sections were counterstained with Mayer hematoxylin (Sigma Ref: MHS32-1L) according to manufacturer's instructions and mounted in aqueous mounting medium for lipids quantification.
H&E Methods:
Paraffin embedded liver samples were sectioned (5 μm thick), dewaxed with a Xylene substitute (Histoclear, National Diagnostics Ref: HS-202) and hydrated through graded alcohol solutions to distilled water. Sections were stained 5 minutes with Harry's hematoxylin (Sigma Ref: HHS128-4L) and 15 minutes with aqueous Eosin (Sigma Ref: HT110232-1L). Samples were dehydrated through graded alcohol solutions and cleared with Histoclear for 10 minutes. Finally sections were mounted in DPX mounting media (Sigma 06522-500 ml).
Sirius Red Methods:
Paraffin embedded liver samples were sectioned (5 μm thick), dewaxed with a Xylene substitute (Histoclear, National Diagnostics Ref: HS-202) and hydrated through graded alcohol solutions to distilled water. Sections were stained with 0.01% Fast green FCF in saturated picric acid for 15 minutes and immediately placed in 0.04% Fast green FCF/0.1% Sirius red in saturated picric acid for 15 minutes. Sections were dehydrated directly in 100% alcohol for 30 seconds and cleared with Histoclear for 10 minutes. Finally sections were mounted in DPX mounting media (Sigma 06522-500 ml).
αSmooth Muscle Actin Immunofluorescence
Dewaxed and rehydrated sections were subjected to antigen retrieval with 10 mM sodium citrate buffer pH 6.0 in a PT link module (DAKO Denmark, Agilent Technologies, Glostrup, Denmark) at 97° C. during 20 minutes with no boil option enabled, then were blocked with goat anti-mouse Fab fragment (Jackson Immunoresearch, West Grove, Pa.) (1 hour, RT, 1:10), followed by 10 minutes incubation with 3% hydrogen peroxide to block endogenous peroxidase activity. Then sections were blocked with 5% normal goat serum in PBS for 30 minutes and incubated with primary Cy3-SMA antibody (1:200) (Sigma Ref: C6198) 1 h at RT. Slides were counterstained with DAPI and mounted with DAKO fluorescence mounting media (DAKO Ref: S3023).
F4/80 Immunohistochemistry:
Dewaxed and rehydrated sections were subjected to antigen retrieval with proteinase K 15 minutes at RT. Endogenous peroxidase activity was blocked with a 10 minutes incubation with 3% hydrogen peroxide, then sections were blocked with 5% normal goat serum in PBS for 30 minutes and incubated with F4/80 primary antibody (1:50, 1 h at 37° C. Bio-rad Ref: MCA497BB) (Bio-rad, Hercules, Calif.) followed by 30 minutes with anti-Rat Immpress reagent (Vector Ref: MP-7404) (Vector Laboratories, Burlingame, Calif.). Colorimetric detection was completed with Vector Vip purple substrate (Vector Ref: sk-4600). Slides were counterstained with Mayer Hematoxylin (Sigma Ref: MHS32-1L) and finally samples were dehydrated through graded alcohol solutions, cleared with Histoclear and mounted in DPX mounting media (Sigma 06522-500 ml).
Glycine N-Methyltransferase (GNMT) (Immunohistochemistry):
Rehydrated sections were blocked with goat anti-mouse Fab fragment (Jackson Immunoresearch) (1 hour, RT, 1:10) and, then, stained with mouse monoclonal anti-GNMT primary antibody (1:400), followed by peroxidase-labeled goat anti-mouse antibody Envision system (DAKO) at room temperature for 3 hours, stained with the peroxidase substrate 3,3 3-diamino-bencidine chromogen (DAKO), and counterstained with hematoxylin.
Intravenous (i.v.) Administration of Anti-miR-873-5p:
Anti-miR-873-5p was synthesized for in vivo studies (Dharmacon). The anti-Mir-875-5p used was purchased from Dharmacon (hsa-miR-873-5p). These hairpin inhibitors are single stranded RNA oligonucleotides designed with a proprietary modification pattern to enhance functionality and target the following sequence in miR-873: gcaggaacuugugagucuccu (SEQ ID NO:1 for human) (miRBase Accession number: MIMAT0004953). These sequences bind and sequester the complimentary, mature microRNA strand, see also Example 1). Invivofectamine 3.0 (Life Technology) was used as a delivery system to obtain high efficiency of in vivo delivery of anti-miRNA into hepatocytes. Following the recommendation of the manufacturer, 1.7 mg/Kg was used in combination with invivofectamine 3.0. Preparation of anti-miRNA with the Invivofectamine was performed as recommended by the manufacturer. Mice were administered twice a week with anti-miRNA/invivofectamine in 150 μl.
qPCR Methods:

2 μs of the obtained RNA were treated with DNase I (Invitrogen) and cDNA was synthesized with M-MLV (Invitrogen) in the presence of random primers and RNaseOUT (Invitrogen). Resulting cDNA was diluted 1/20 in RNase free water (Sigma-Aldrich), and 5 microliter were used for PCR reaction. PCRs were performed using BioRad iCycler iQ5 Thermalcycler, with iQ SYBR Green Super Mix (Bio Rad) and specific primers, in a total reaction volume of 20 μl, and all reactions were performed in triplicates. PCR conditions for these primers were optimized, and 40 cycles with a melting temperature of 60° C., and 30 sec of each step, were used. Primers were designed using Primer 3 Software and synthetized by Sigma-Aldrich. After checking the specificity of the PCR products with the melting curve, Ct values were extrapolated to a standard curve performed simultaneously with the samples and data was then normalized to the expression of a housekeeping gene (GAPDH).

microRNA Quantitative Real-Time PCR

Specific RT-PCR was performed for miR-873-5p following TagMan® MicroRNA Reverse Transcription Kit procedure. 10-50 ng of RNA were used for the reaction. qPCR was performed with TaqMan Universal PCR Master Mix No AmpErase UNG kit (Life Technologies) and specific primers for miR-873-5p following manufacturers procedure. miR-873-5p was normalized with the U6 snRNA.

Animals

Three-month-old male C57BL/6 mice were used in the study Animal procedures were approved following the CIC bioGUNE Animal Facility's guidelines with AAALAC certificate. Mice were fed with standard maintenance diet, methionine and choline deficient diet (MCDD), high fat diet (HFD) or high cholesterol diet (HCD).

Blood Sampling Method and Sample Handling.

Submandibular blood samples were obtained by incising the right submandibular vein of unanesthetized mice with a sterile 4-mm lancet (MediPoint, Mineola, N.Y.). Retroorbital blood samples were collected from the right retroorbital plexus of anesthetized mice. Anesthesia was induced by placing each mouse in an inhalation chamber with 4% isoflurane (IsoFlo, Abbott Laboratories, Berkshire, UK) regulated with a calibrated vaporizer. Blood samples were deposited in serum separator gel tubes (Microtainer, Becton-Dickinson, Franklin Park, N.J.) and centrifuged (9,300×g, 15 min, 4° C.) for serum separation.

Clinical Chemistry Parameters.

A panel of serum biochemistries was conducted and included aspartate aminotransferase (AST-GOT), alanine aminotransferase (ALT-GPT), triglycerides, glucose, cholesterol, protein and albumin. The samples were analyzed using a Selectra Junior Spinlab 100 analyser (Vital Scientific, Dieren, Netherland) according to manufacturers' suggested protocol. Calibrated controls were run before each use and were within established ranges prior to analyzing samples.

Quantification of Total Lipids

Livers (300 mg) were homogenized and lipids extracted as described by Bligh, E. G., and W. J. Dyer (1959) Can J Biochem Physiol. August; 37(8):911-7. TGs were quantified using a kit according to manufacturer's instructions (A. Menarini Diagnostics, Italy). Serum was extracted from blood and ketone bodies were quantified using a commercially available kit from Wako chemicals GmbH (Richmond, Va.) using manufacturer's instructions. The kits used for ketone body quantification was the following, which has two components, and a calibrator kit): Autokit T-KB R1 Set ref 415-73301, Autokit T-KB R2 Set Ref 413-73601; and the Ketone body calibrator 300 Ref 412-73791.

Results miR-873-5p Expression in NAFLD.

Figure 9B:
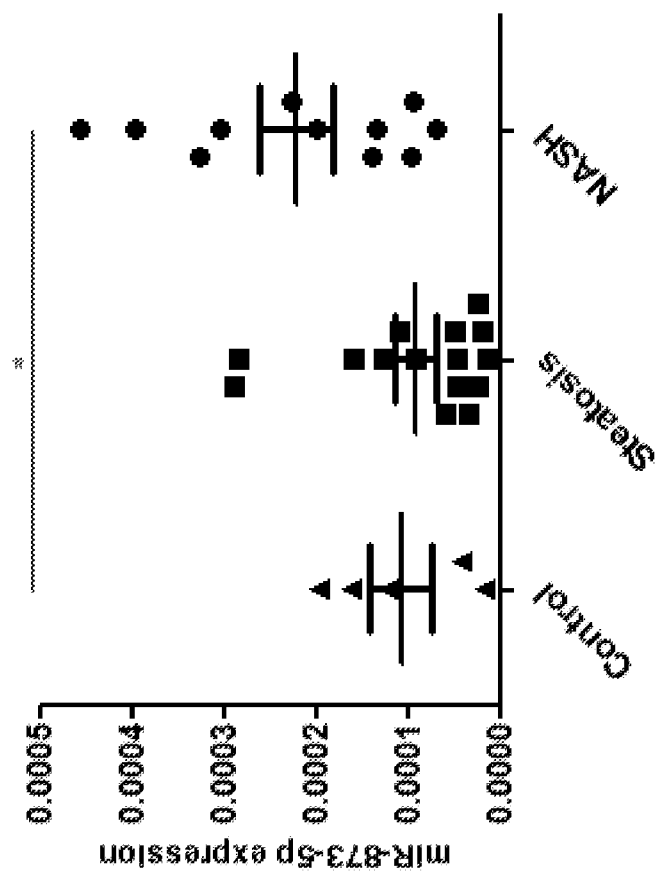
FIG. 9A-D provides graphs showing miR-873-5p expression in NAFLD.
Figure 9A:
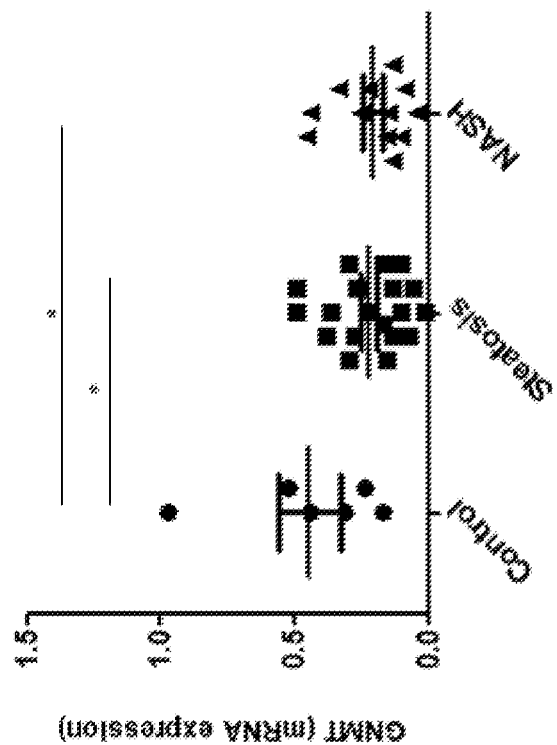
Figure 9D:
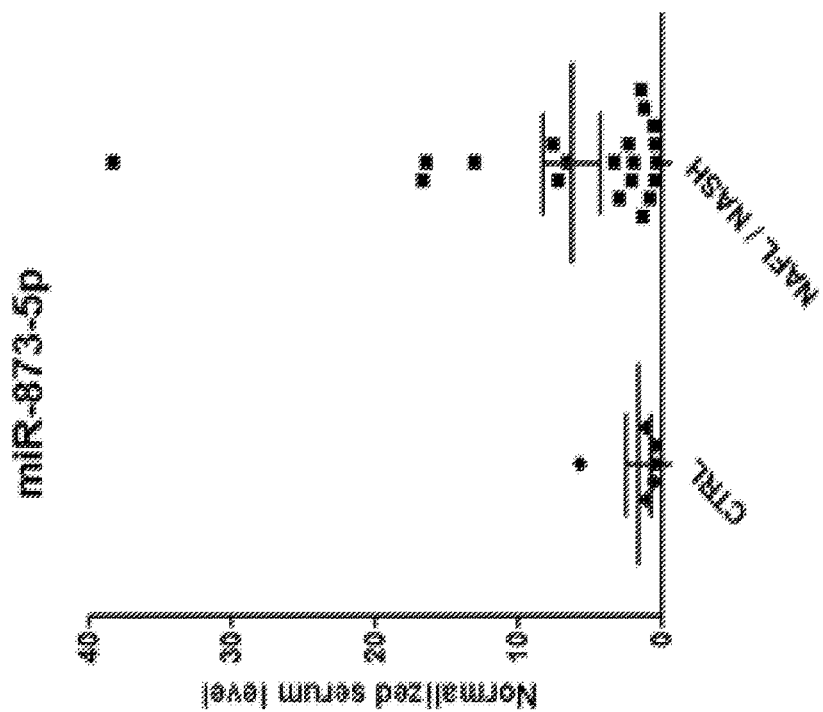
Figure 9C:
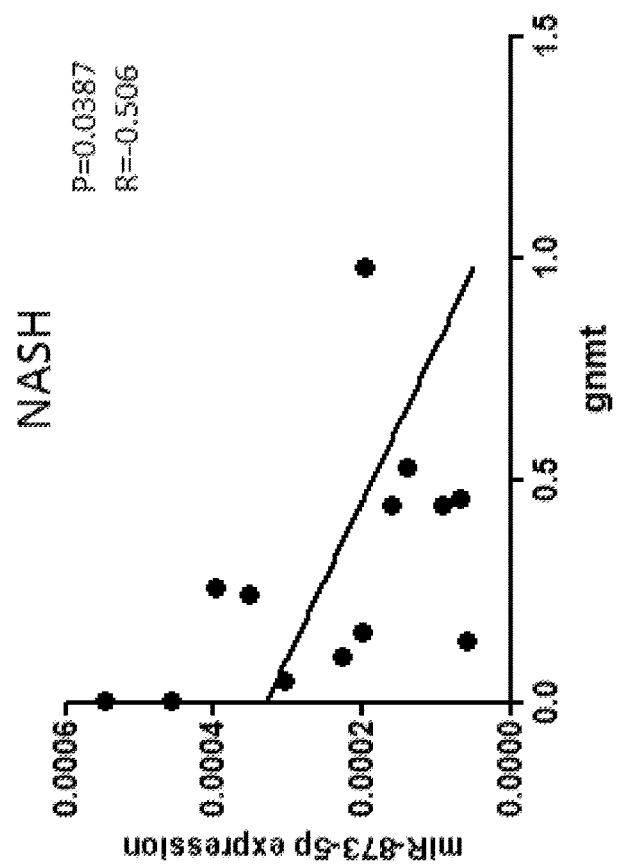

GNMT expression and SAMe metabolism is markedly impaired in patients with steatosis and steatohepatitis. Using qPCR, GNMT and miR-873-5p expression were measured in liver samples of healthy control patients and NAFLD patients, revealing a decrease of GNMT accompanied by an increase of miR-873-5p levels (FIG. 9A-B). In addition, a significant an inverse correlation between GNMT-miR-873 levels has been identified (FIG. 9C). Finally, miR-873-5p levels were found to be increased in serum samples from patients suffering NAFLD compared to healthy control patients (FIG. 9D).

miR-873-5p Expression in NAFLD Mice Models.

Figure 10A:
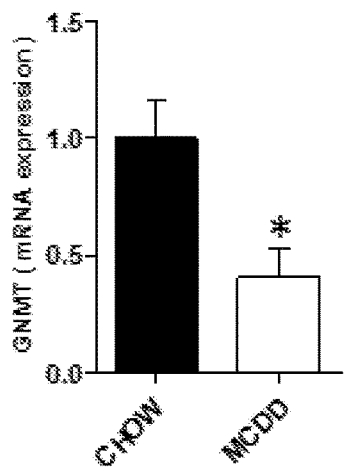
FIG. 10A-C provides graphs showing miR-873-5p expression in NAFLD mice models.
Figure 10A:
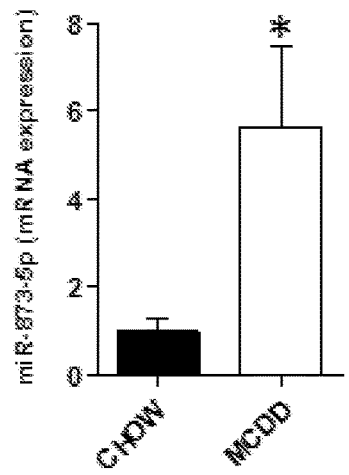
Figure 10B:
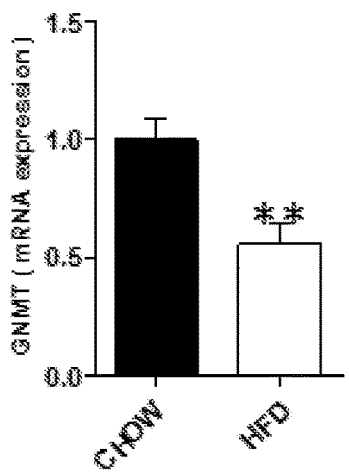
Figure 10B:
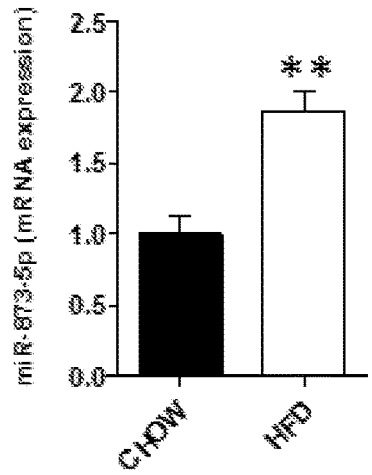
Figure 10C:
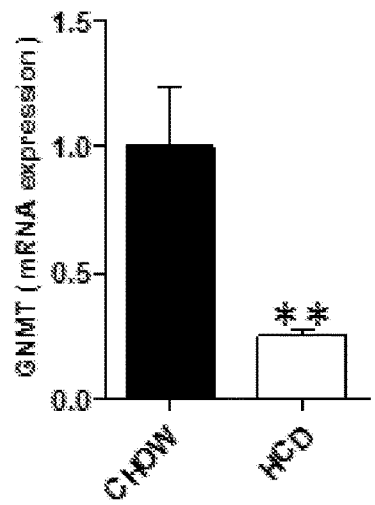
Figure 10C:
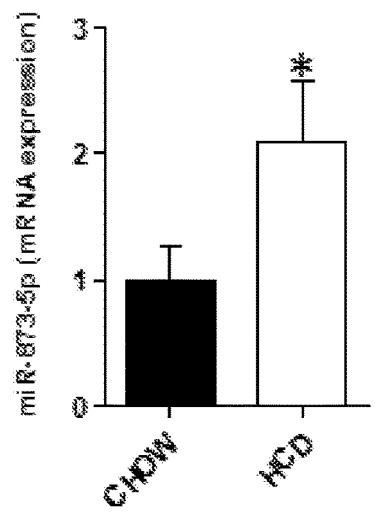

In order to study the role of GNMT/miR-873 regulation in the development of fatty liver, both GNMT and miR-873-5p expression levels were measured in different NAFLD mice models. Mice were fed with standard maintenance diet, methionine and choline deficient diet (MCDD, FIG. 10A), high fat diet (HFD, FIG. 10B) or high cholesterol diet (HCD FIG. 10C). In all the studied diets an inverse correlation between GNMT and miR-873-5p expression was observed, indicating a role of miR-873-5p in the development of NAFLD.

Inhibition of the miR-873-5p in MCDD Counteracts NAFLD Development.

Figure 11A:
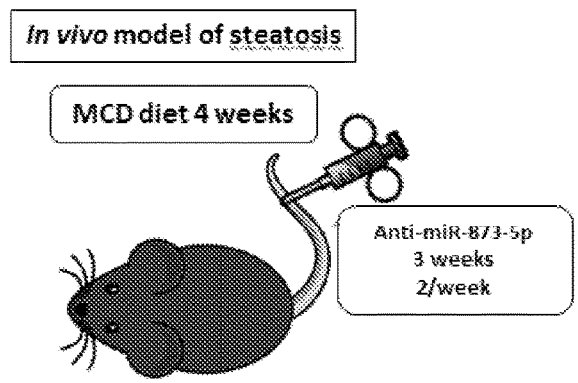
FIG. 11A-G provides a schematic diagram, photomicrographic images and graphs demonstrating that inhibition of the miR-873-5p in MCDD counteracts NAFLD. Mice in the studies were fed with MCDD during four weeks and anti-miR-873-5p was tail injected during 3 weeks.
Figure 11B:
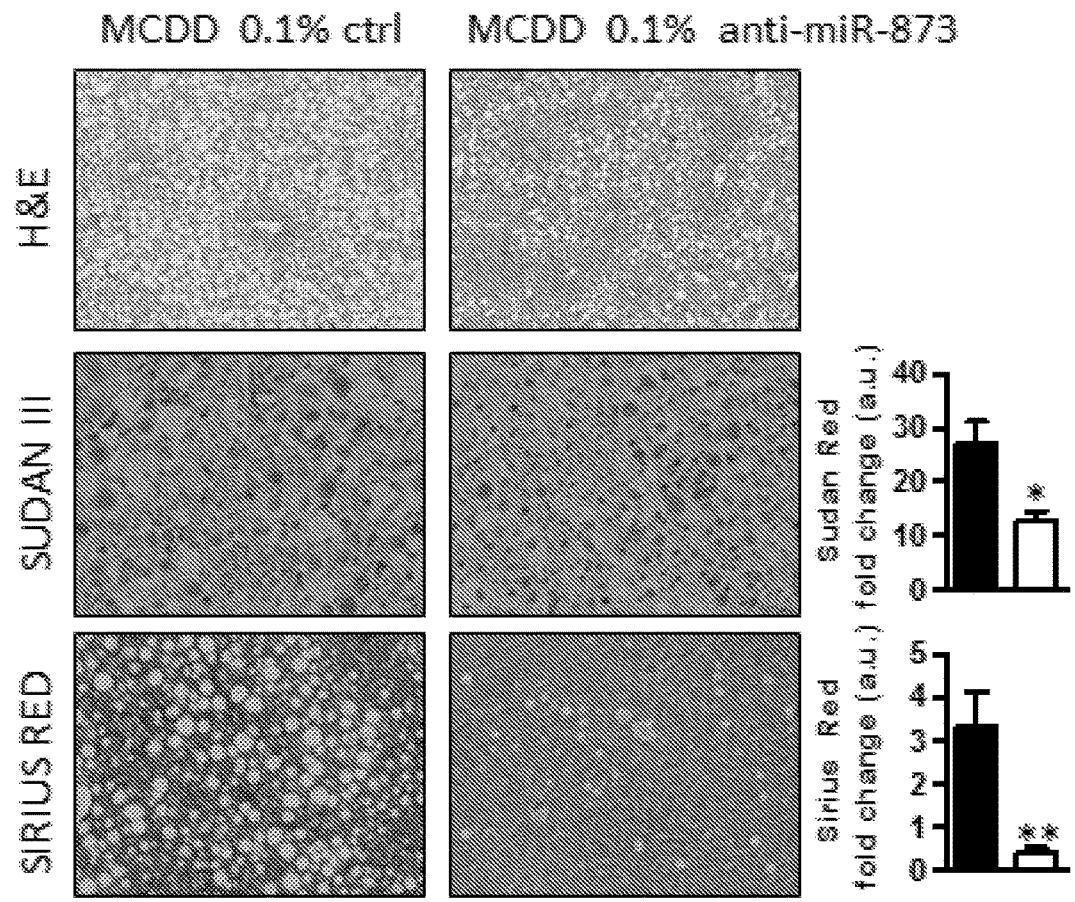
Figure 11C:
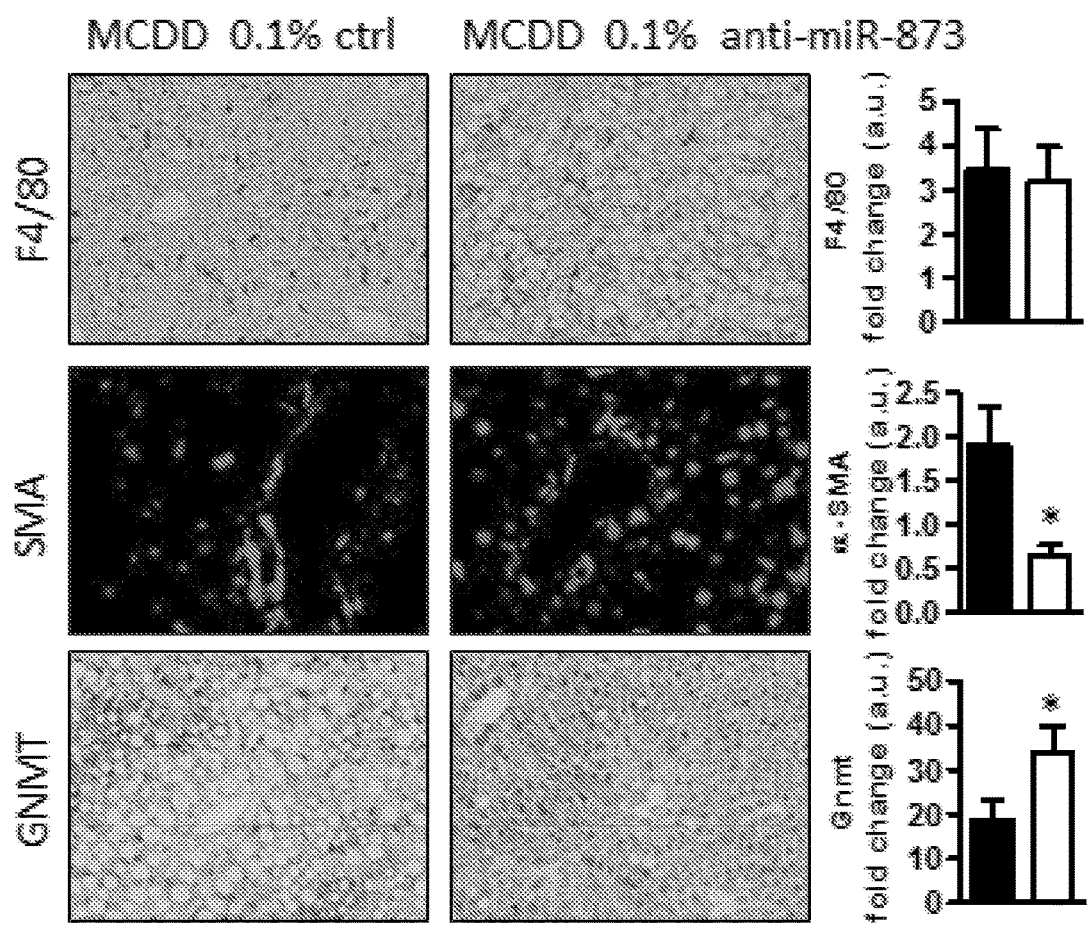
Figure 11D:
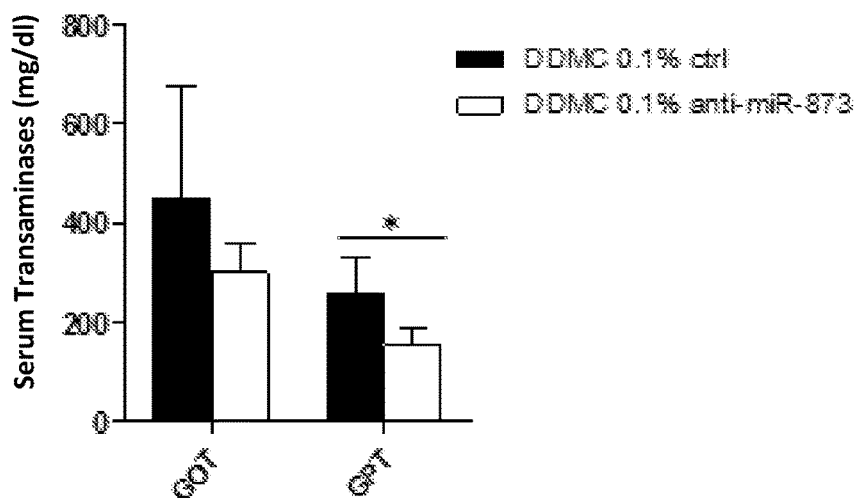
Figure 11E:
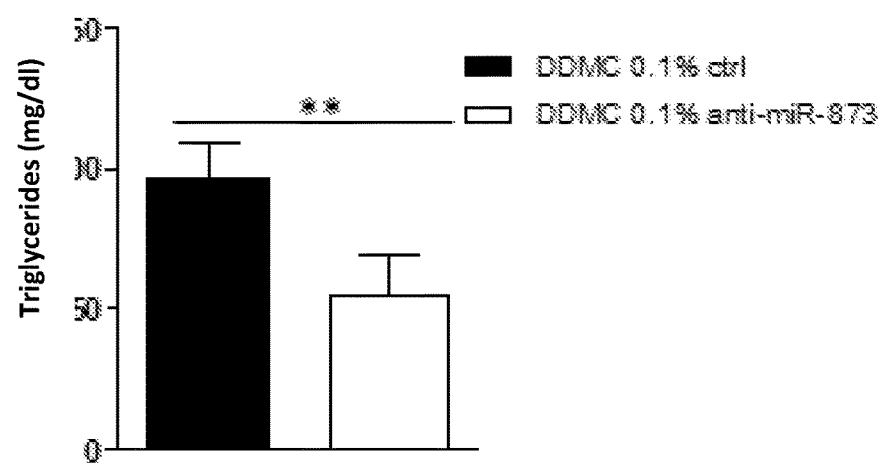
Figure 11F:
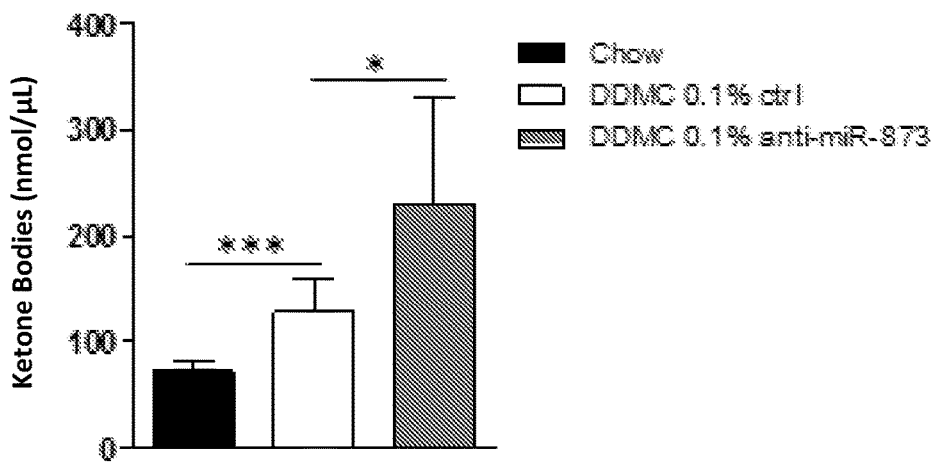
Figure 11G:
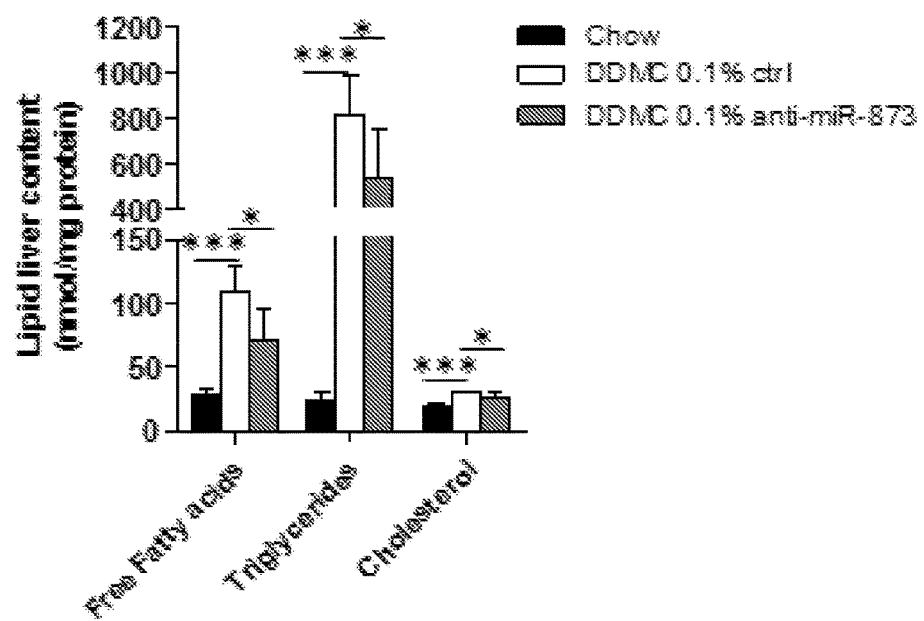

To study the role of miR-873-5p in NAFLD, mice were fed MCD diet for 4 weeks and miR-873-5p was inhibited with specific anti-miR-873-5p by tail vein injection twice a week for 3 weeks. Final characterization by immunohistochemistry (IHC) of miR-873-inhibited mice after MCD diet show lower amounts of hepatic lipid content (Sudan Red), as well as decrease of proinflammatory and profibrogenic markers (F4/80, Sirius Red and αSMA). These results were accompanied by increased GNMT levels compared to control MCD diet mice (FIG. 11A-C). Moreover, analyses of serum collected from MCD diet mice showed a decrease of hepatic transaminases levels (GOT, GPT) in anti-miR-873-5p-treated mice indicating a less injured liver. Other serum markers revealed a decrease in triglycerides alongside an increase of the ketone bodies (FIG. 11D-F), indicating a reduced export of triglycerides from the liver to the blood and an increase in fatty acid oxidation in the liver with the consequent increase of ketone bodies in blood. Finally, total lipid content of these livers was analyzed. In this case, the study showed that miR-873 inhibition mediates a significant reduction of different lipids in the liver at the end of the MCD diet, showing lower content of free fatty acids, triglycerides and cholesterol (FIG. 11G).

DISCUSSION

The metabolic syndrome is a cluster of clinical factors: diabetes, abdominal obesity, high cholesterol and high blood pressure. It is estimated that around 20-25 percent of the world's adult population have the metabolic syndrome and they are twice as likely to die from and three times as likely to have a heart attack or stroke compared with people without the syndrome. In addition, people with metabolic syndrome have a fivefold greater risk of developing type 2 diabetes. Each year, 3.2 million people around the world die from complications associated with diabetes. Moreover, obesity has become a world-wide epidemic. For the first time in human history, the number of overweight people rivals the number of underweight people. Globally there are >1 billion overweight adults with about 300 million clinically obese. Obesity is responsible for 2-8% of healthcare costs and 10-13% of deaths in different parts of EU. Non-alcoholic fatty liver disease (NAFLD) is the most common liver disease since its prevalence is estimated to be 20-30% in general population of Western countries. It has been shown that NAFLD is strongly associated to the features of metabolic syndrome. Insulin resistance is a key pathogenic factor in both NAFLD and metabolic syndrome. Available data from clinical, experimental and epidemiological studies indicate that NAFLD may be the hepatic manifestation of metabolic syndrome.

Glycine N-methyltransferase (GNMT) is an essential regulator of the total transmethylation flux in the mammalian liver. Distinct DNA methylation patterns are characteristic of liver development, hepatic de-differentiation and liver disease progression, among them NAFLD, fibrosis, cirrhosis and liver cancer, processes in which the levels of GNMT decrease dramatically by mechanisms still poorly understood [Avila M A, et al., (2000) *J. Hepatol.* 33:907-9141].

MicroRNAs (miRNA) are an emerging class of highly conserved, non-coding small RNAs that regulate gene expression both by RNA silencing or at the post-transcriptional level [Filipowicy w., et al., (2005) *Curr. Opin Struct. Biol.* 15:331-341]. miRNAs regulate essential biological processes including differentiation and metabolism, as well as cellular responses like proliferation, apoptosis and tumorigenesis [Meltzer, P. S. (2005) *Nature* 435:745-74]. In the liver, miRNAs signature has been implicated in non-alcoholic fatty liver disease (NAFLD), cirrhosis and liver cancer [Croce, C. M. (2008) *N. Engl. J. Med* 358:502-511].

Interestingly, putative binding sites for the microRNA miRNA-873-5p were identified in the 3'UTR of GNMT suggesting a potential role for miRNA-873-5p in GNMT regulation. It has now been identified that the hepatic expression of miRNA-873-5p was increased in a cohort of NAFLD patients. Under these circumstances, inhibition of miRNA-873-5p induced GNMT levels. Indeed, reestablishment of GNMT expression by miRNA-873-5p inhibition reduced the development of steatosis and steatohepatitis in mice under a steatotic diet. Taken together, the results highlight the role of miRNA-873-5p as a new therapeutic approach in NAFLD and other liver diseases.

Example 3

Inhibition of miRNA-518d-5p

Experiments are also performed using an anti-miR-518-5p (Dharmacon). See methods in Examples 1 and 2 herein. The anti-Mir-518-5p is obtained from Dharmacon (hsa-miR-518-5p). These hairpin inhibitors are single stranded RNA oligonucleotides designed with a proprietary modification pattern to enhance functionality and target the following sequence in miR-518: cucuagagggaagcacuuucug (SEQ ID NO: 8 for human) (miRBase Accession number: MIMAT0005456). The anti-miR sequence binds and sequesters the complimentary, mature microRNA strand, see also Examples 1 and 2. Inhibition experiments are performed as indicated in Examples 1 and 2 herein. The experiments demonstrate that inhibition of miR-518d-5p induces GNMT levels. The reestablishment of GNMT expression by miRNA-518d-5p inhibition reduces the development of steatosis and steatohepatitis in mice under a steatotic diet. Taken together, the results highlight the role of miRNA-518d-5p as a therapeutic approach in NAFLD and other liver diseases.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

The invention claimed is:

1. A method of increasing glycine N-methyltransferase (GNMT) enzyme activity in a cell, the method comprising contacting a cell with an miRNA-inhibitor compound that inhibits at least one of miRNA-873-5p and miRNA-518d-5p in an amount effective to increase GNMT enzyme activity in the cell, wherein the increase in GNMT enzyme activity reduces DNA hypermethylation in the cell.

2. The method of claim 1, wherein the cell is in a subject and the contacting comprises administering the miRNA-inhibitor compound to the subject.

3. The method of claim 2, wherein the miRNA-inhibitor compound is administered in a pharmaceutical composition and the pharmaceutical composition further comprises a pharmaceutically acceptable carrier.

4. The method of claim 1, wherein the miRNA-inhibitor compound further comprises one or more of a detectable label and a targeting agent, wherein optionally the targeting agent is a liver targeting agent.

5. The method of claim 1, wherein the miRNA-inhibitor compound comprises one or more of an RNA molecule, an miRNA sponge compound, an antisense inhibitor compound, and a modified miRNA molecule.

6. The method of claim 1, wherein the miRNA-inhibitor compound inhibits miRNA-873-5p.

7. The method of claim 1, wherein the cell is a liver cell.

8. The method of claim 1, wherein the cell is one or more of a liver cancer cell, a metastatic cancer cell, a precancerous liver cell, a cirrhotic liver cell, a post-cancer liver cell, a fibrotic liver cell, a hepatocyte, an inflammatory liver cancer cell, and a chemoresistant liver cell.

9. The method of claim 1, wherein the cell is not a cancer cell.

10. The method of claim 1, further comprising contacting the cell with one or more additional therapies for treatment of a liver cancer, a metastatic cancer, a precancerous liver condition, hepatocellular carcinoma, cirrhosis, a post-cancer liver condition, non-alcoholic fatty liver disease (NAFLD), liver cancer, a metastatic cancer in the liver, a precancerous liver condition, hepatocellular carcinoma, cirrhosis, a post-cancer liver condition, non-alcoholic steatohepatitis (NASH), cryptogenic cirrhosis, hepatocelullar carcinoma, liver decompensation, steatohepatitis, and chemoresistance.

11. The method of claim 1, wherein the miRNA-inhibitor compound reduces de-differentiation of the contacted cell.

12. The method of claim 1, wherein the miRNA-inhibitor compound inhibits miRNA-518d-5p.

13. The method claim 10, wherein the cell is contacted with the one or more additional therapies at one of more of times before, coincident with, and after the cell is contacted with the miRNA-inhibitor compound.

14. The method of claim 10, wherein the one or more additional therapies are independently selected from radiation therapy, surgery, chemotherapy, molecular-targeted cancer therapy, cytostatic therapy, and cytotoxic therapy.

* * * * *

SEQUENCE LISTING

<160> NUMBER OF SEQ ID NOS: 15

<210> SEQ ID NO 1
<211> LENGTH: 21
<212> TYPE: RNA
<213> ORGANISM: Homo sapiens

```
<220> FEATURE:
<221> NAME/KEY: misc_feature
<223> OTHER INFORMATION: hsa-miR-873-5p

<400> SEQUENCE: 1
gcaggaacuu gugagucucc u                                              21

<210> SEQ ID NO 2
<211> LENGTH: 21
<212> TYPE: RNA
<213> ORGANISM: Mus musculus
<220> FEATURE:
<221> NAME/KEY: misc_feature
<223> OTHER INFORMATION: mmu-miR-873a-5p

<400> SEQUENCE: 2
gcaggaacuu gugagucucc u                                              21

<210> SEQ ID NO 3
<211> LENGTH: 21
<212> TYPE: RNA
<213> ORGANISM: Rattus novergicus
<220> FEATURE:
<221> NAME/KEY: misc_feature
<223> OTHER INFORMATION: rno-miR-873-5p

<400> SEQUENCE: 3
gcaggaacuu gugagucucc u                                              21

<210> SEQ ID NO 4
<211> LENGTH: 21
<212> TYPE: RNA
<213> ORGANISM: Populus trichocarpa
<220> FEATURE:
<221> NAME/KEY: misc_feature
<223> OTHER INFORMATION: ptr-miR-873

<400> SEQUENCE: 4
gcaggaacuu gugagucucc u                                              21

<210> SEQ ID NO 5
<211> LENGTH: 21
<212> TYPE: RNA
<213> ORGANISM: Bos taurus
<220> FEATURE:
<221> NAME/KEY: misc_feature
<223> OTHER INFORMATION: bta-miR-873

<400> SEQUENCE: 5
gcaggaacuu gugagucucc u                                              21

<210> SEQ ID NO 6
<211> LENGTH: 21
<212> TYPE: RNA
<213> ORGANISM: Equus caballus
<220> FEATURE:
<221> NAME/KEY: misc_feature
<223> OTHER INFORMATION: eca-miR-873

<400> SEQUENCE: 6
gcaggaacuu gugagucucc u                                              21

<210> SEQ ID NO 7
<211> LENGTH: 21
<212> TYPE: RNA
<213> ORGANISM: Pongo pygmaeus
```

```
<220> FEATURE:
<221> NAME/KEY: misc_feature
<223> OTHER INFORMATION: ppy-miR-873

<400> SEQUENCE: 7
gcaggaacuu gugagucucc u                                             21

<210> SEQ ID NO 8
<211> LENGTH: 22
<212> TYPE: RNA
<213> ORGANISM: Homo sapiens
<220> FEATURE:
<221> NAME/KEY: misc_feature
<223> OTHER INFORMATION: hsa-miRNA-518d-5p

<400> SEQUENCE: 8
cucuagaggg aagcacuuuc ug                                            22

<210> SEQ ID NO 9
<211> LENGTH: 22
<212> TYPE: RNA
<213> ORGANISM: Homo Sapiens
<220> FEATURE:
<221> NAME/KEY: misc_feature
<223> OTHER INFORMATION: hsa-miR-526a

<400> SEQUENCE: 9
cucuagaggg aagcacuuuc ug                                            22

<210> SEQ ID NO 10
<211> LENGTH: 22
<212> TYPE: RNA
<213> ORGANISM: Homo Sapiens
<220> FEATURE:
<221> NAME/KEY: misc_feature
<223> OTHER INFORMATION: hsa-miR-520c-5p

<400> SEQUENCE: 10
cucuagaggg aagcacuuuc ug                                            22

<210> SEQ ID NO 11
<211> LENGTH: 22
<212> TYPE: RNA
<213> ORGANISM: Populus trichocarpa
<220> FEATURE:
<221> NAME/KEY: misc_feature
<223> OTHER INFORMATION: ptr-miR-526a

<400> SEQUENCE: 11
cucuagaggg aagcacuuuc ug                                            22

<210> SEQ ID NO 12
<211> LENGTH: 22
<212> TYPE: RNA
<213> ORGANISM: Gorilla gorilla
<220> FEATURE:
<221> NAME/KEY: misc_feature
<223> OTHER INFORMATION: ggo-miRNA-518d-5p

<400> SEQUENCE: 12
cucuagaggg aagcacuuuc ug                                            22

<210> SEQ ID NO 13
<211> LENGTH: 22
<212> TYPE: RNA
<213> ORGANISM: Gorilla gorilla
```

```
<220> FEATURE:
<221> NAME/KEY: misc_feature
<223> OTHER INFORMATION: ggo-miR-520cd

<400> SEQUENCE: 13
cucuagaggg aagcacuuuc ug                                              22

<210> SEQ ID NO 14
<211> LENGTH: 22
<212> TYPE: RNA
<213> ORGANISM: Gorilla gorilla
<220> FEATURE:
<221> NAME/KEY: misc_feature
<223> OTHER INFORMATION: ggo-miR-526a

<400> SEQUENCE: 14
cucuagaggg aagcacuuuc ug                                              22

<210> SEQ ID NO 15
<211> LENGTH: 22
<212> TYPE: RNA
<213> ORGANISM: Pongo pygmaeus
<220> FEATURE:
<221> NAME/KEY: misc_feature
<223> OTHER INFORMATION: ppy-miRNA-518g-5p

<400> SEQUENCE: 15
cucuagaggg aagcacuuuc ug                                              22
```